(12) United States Patent
Scott et al.

(10) Patent No.: US 8,017,361 B2
(45) Date of Patent: Sep. 13, 2011

(54) ENZYMATIC HYDROLYSIS OF LIGNOCELLULOSIC FEEDSTOCKS USING ACCESSORY ENZYMES

(75) Inventors: Brian R. Scott, Ontario (CA); Christopher Hill, Ontario (CA); John Tomashek, Ontario (CA); Chengsong Liu, Ontario (CA)

(73) Assignee: Iogen Energy Corporation, Ontario (CA)

( * ) Notice: Subject to any disclaimer, the term of this patent is extended or adjusted under 35 U.S.C. 154(b) by 363 days.

(21) Appl. No.: 12/201,374

(22) Filed: Aug. 29, 2008

(65) Prior Publication Data

US 2009/0061484 A1 Mar. 5, 2009

Related U.S. Application Data

(60) Provisional application No. 60/969,046, filed on Aug. 30, 2007.

(51) Int. Cl.
| | |
|---|---|
| C12P 19/14 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl. .... 435/99; 435/183; 435/252.3; 435/320.1; 536/23.2

(58) Field of Classification Search .......... None
See application file for complete search history.

(56) References Cited

U.S. PATENT DOCUMENTS

| | | | |
|---|---|---|---|
| 4,461,648 | A | 7/1984 | Foody |
| 5,763,254 | A | 6/1998 | Woldike et al. |
| 6,015,703 | A | 1/2000 | White et al. |
| 7,348,168 | B2 | 3/2008 | Wu et al. |
| 2003/0104546 | A1 | 6/2003 | Swanson et al. |
| 2004/0197890 | A1 | 10/2004 | Lange et al. |
| 2005/0277172 | A1 | 12/2005 | Day et al. |
| 2006/0053514 | A1 | 3/2006 | Wu et al. |
| 2006/0057672 | A1 | 3/2006 | Bower et al. |
| 2006/0205042 | A1 | 9/2006 | Aehle et al. |
| 2007/0238155 | A1 | 10/2007 | Gusakov et al. |
| 2008/0057541 | A1* | 3/2008 | Hill et al. .............. 435/72 |
| 2010/0184151 | A1* | 7/2010 | Tolan et al. ............ 435/72 |

FOREIGN PATENT DOCUMENTS

| | | |
|---|---|---|
| CA | 2541229 | 9/2006 |
| WO | 02/24882 | 3/2002 |
| WO | 03/078644 | 9/2003 |
| WO | 2005/001036 | 1/2005 |
| WO | 2005/074647 | 8/2005 |
| WO | 2005/074656 | 8/2005 |
| WO | 2007/147263 | 12/2007 |
| WO | 2008/025165 | 3/2008 |

OTHER PUBLICATIONS

Berlin, et al. "Optimization of Enzyme Complexes for Lignocellulose Hydrolysis", Biotechnology and Bioengineering, vol. 97, No. 2 (2007) 287-96.
Sorenson, et al., "Enzymatic Hydrolysis of Wheat Arabinoxylan by a Recombinant "Minimal" Enzyme Cocktail Containing Beta-Xylosidase and Novel endo-1,4-Beta-Xylanase and alpha-L-Arabinofuranosidase Activities", Biotechnol. Prog., vol. 23 (2007) 100-7.
Saloheimo, et al. "Swollenin, a *Trichoderma reesei* protein with sequence similarity to the plant expansins, exhibits disruption activity on cellulosic materials", Eur. J. Biochem., vol. 269 (2002) 4202-11.
Karlsson, et al., "Homologous expression and characterization of Cel61A (EG IV) of *Trichoderma reesei*", Eur. J. Biochem., vol. 268 (2001) 6498-507.
Foreman, et al., "Transcriptional Regulation of Biomass-degrading Enzymes in the Filamentous Fungus *Trichoderma reesei*", J. Biol. Chem., vol. 278, No. 34 (2003) 31988-997.
Lynd, et al., "Microbial Cellulose Utilization: Fundamentals and Biotechnology", Microbiol. and Molec. Biol. Rev., vol. 66, No. 3 (2002) 506-77.
Desmet, et al., "An investigation of the substrate specificity of the xyloglucanase Cel74A from *Hypocrea jecorina*", FEBS J., vol. 274 (2007) 356-63.
Karlsson, et al., "Enzymatic properties of the low molecular mass endoglucanases Cel12A (EG III) and Cel45A (EG V) of *Trichoderma reesei*", J. Biotech., vol. 99 (2002) 63-78.

\* cited by examiner

*Primary Examiner* — Christian Fronda
(74) *Attorney, Agent, or Firm* — Fitzpatrick, Cella, Harper & Scinto

(57) ABSTRACT

Provided is an enzyme mixture for hydrolyzing a pretreated lignocellulosic feedstock to soluble sugars. The enzyme mixture comprises EG4 at a fractional concentration ($f_{EG4}$) of about 0.25 to about 0.83 (w/w), Swollenin at a fractional concentration ($f_{Swo1}$) of about 0 to about 0.66 (w/w), and Cip1 at a fractional concentration ($f_{Cip1}$) of 0 to about 0.33 measured relative to all accessory enzymes present in the enzyme mixture. Also provided are processes for converting a pretreated lignocellulosic feedstock to soluble sugars using the enzyme mixtures, and methods of using and producing such enzyme mixtures.

45 Claims, 7 Drawing Sheets

Zone 1

$0.25 \leq f_{EG4} \leq 0.83$ $0.00 \leq f_{Swo1} \leq 0.66$ $0.00 \leq f_{Cip1} \leq 0.33$ Zone 2

$0.33 \leq f_{EG4} \leq 0.50$ $0.33 \leq f_{Swo1} \leq 0.58$ $0.08 \leq f_{Cip1} \leq 0.25$

ENZYMATIC HYDROLYSIS OF LIGNOCELLULOSIC FEEDSTOCKS USING ACCESSORY ENZYMES

RELATED APPLICATIONS

This application claims the priority benefit of a provisional application entitled THE USE OF ACCESSORY ENZYMES IN A PROCESS FOR THE ENZYMATIC HYDROLYSIS OF PRETREATED LIGNOCELLULOSIC FEEDSTOCKS, Application No. 60/969,046, filed Aug. 30, 2007, the entire contents of which are incorporated herein by reference.

FIELD OF THE INVENTION

The present invention provides a cellulase enzyme mixture. The present invention also provides a process for the hydrolysis of a lignocellulosic feedstock using the cellulase enzyme mixture.

BACKGROUND OF THE INVENTION

Lignocellulosic feedstocks are a promising alternative to corn starch for the production of fuel ethanol. Lignocellulosic feedstocks are widely available, inexpensive and several studies have concluded that cellulosic ethanol generates close to zero greenhouse gas emissions.

However, lignocellulosic feedstocks are not easily broken down into their composite sugar molecules. Recalcitrance of lignocellulose can be partially overcome by physical and/or chemical pretreatment. An example of a chemical pretreatment is steam explosion in the presence of dilute sulfuric acid, (U.S. Pat. No. 4,461,648). This process removes most of the hemicellulose, but there is little conversion of the cellulose to glucose. The pretreated material may then be hydrolyzed by cellulase enzymes.

The term cellulase (or cellulase enzymes) broadly refers to enzymes that catalyze the hydrolysis of the β-1,4-glucosidic bonds joining individual glucose units in the cellulose polymer. The catalytic mechanism involves the synergistic actions of endoglucanases (E.C. 3.2.1.4), cellobiohydrolases (E.C. 3.2.1.91) and β-glucosidase (E.C. 3.2.1.21). Endoglucanases hydrolyze accessible glucosidic bonds in the middle of the cellulose chain, while cellobiohydrolases release cellobiose from these chain ends processively. β-Glucosidases hydrolyze cellobiose to glucose and, in doing so, minimize product inhibition of the cellobiohydrolases. Collectively, the enzymes operate as a system that can hydrolyze a cellulose substrate.

Cellulase enzymes may be obtained from filamentous fungi, including *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Fusarium* ssp., *Penicillium* ssp., *Magnaporthe* ssp. and *Phanerochaete* ssp.

*Trichoderma* spp. (*Trichoderma longibrachiatum* or *Trichoderma reesei*) produce cellulase enzymes able to degrade crystalline cellulose. *Trichoderma reesei* secretes two cellobiohydrolases, CBH1 (Cel7A) and CBH2 (Cel6A), which release cellobiose from reducing and non-reducing ends of the cellulose chain, respectively, and β-Glucosidase (Cel3A). EG1 (Cel7B) and EG2 (Cel5A) are two major endocellulases involved in the hydrolysis of crystalline cellulose. CBH1 (Cel7A), CBH2 (Cel6A), EG1 (Cel7B) and EG2 (Cel5A) comprise two functional domains—a catalytic domain and a carbohydrate binding module (CBM).

Of the remaining endoglucanases, EG3 (Cell2A) lacks a carbohydrate binding module and therefore binds crystalline cellulose poorly (Karlsson et al., *Journal of Biotechnology*, 99:63-78, (2002)). EG5 (Cel45A) and EG6 (Cel74A) are reported to be a glucomannanase (Karlsson et al., 2002a) and a xyloglucanase (Desmet et al., *FEBS Journal*, 274:356-363, (2006)), respectively. EG4 (Cel61A) reportedly exhibits some activity on carboxymethyl cellulose, hydroxyethyl cellulose and β-glucan (Karlsson et al., *European Journal of Biochemistry*, 268:6498-6507, (2002b)). However, when compared to EG1, the specific activity of EG4 on these substrates was four orders of magnitude lower, suggesting that its native substrate and/or mode of action lie elsewhere. Nonetheless, the addition of Cel61A from *Thermoascus aurantiacus* to *Trichoderma* cellulase has reportedly improved the hydrolysis of pretreated corn stover (WO 2005/074656). This has also been shown for Cel61B, Cel61C and Cel61D from *Thielavia terrestris* (WO 2005/074647).

The enzymatic hydrolysis of pretreated lignocellulosic feedstocks is an inefficient step in the production of cellulosic ethanol and its cost constitutes one of the major barriers to commercial viability. Improving the enzymatic activity of cellulases or increasing cellulase production efficiency has been widely regarded as an opportunity for significant cost savings.

Numerous approaches have been taken to improve the activity of cellulase for ethanol production. The amount of β-glucosidase activity secreted by *Trichoderma* has been increased in order to minimize cellobiose accumulation and product inhibition (U.S. Pat. No. 6,015,703). Mutagenesis strategies have been used to improve the thermal stability of CBH1 (US 2005/0277172) and CBH2 (US 2006/0205042). Amino acid consensus and mutagenesis strategies have been employed to improve the activity of CBH1 (US 2004/0197890) and CBH2 (US 2006/0053514). A fusion protein consisting of the Cel7A catalytic domain from *T. reesei* and the EG1 catalytic domain from *Acidothermus cellulolyticus* has been constructed (US 2006/0057672). Additionally, novel combinations of CBMs and catalytic domains from cellulases and hemicellulases originating from *Myceliopthora*, *Humicola* and *Fusarium* have been generated by domain shuffling in an attempt to generate enzymes with novel enzyme specificities and activities (U.S. Pat. No. 5,763,254).

These approaches focused on individual cellulase components, in particular those exhibiting substantial activity on laboratory substrates such as filter paper, CMC, HEC and β-glucan. While altering the properties of an individual protein, these approaches have not increased substantially the activity of the whole cellulase enzyme system and, therefore, have not reduced the cost of enzyme required for the production of cellulosic ethanol.

Some studies have tested hemicellulases in conjunction with a cellulase preparation for improved activity on lignocellulosic substrates (Berlin et al., *Biotechnology and Bioengineering*, 97(2): 287-296, (2007)). However, effective pretreatments of lignocellulosic feedstocks, such as the steam explosion process, remove virtually all of the hemicellulose, strongly suggesting that improving hemicellulase activity is not the best approach to reduce cellulase costs.

Some *Trichoderma* cellulase components have negligible hydrolytic activity on laboratory cellulose-mimetic substrates, but are induced by cellulose. Cip1 and Cip2 are induced by cellulose and sophorose, implying that they have roles in the breakdown of cellulosic biomass, yet their activities are unknown (Foreman et al., *Journal of Biological Chemistry*, 278(34) 31988-31997, (2003)). Swollenin (Swo1), a novel fungal protein containing an expansin domain and a CBM, has been shown to disrupt cotton fibers (Saloheimo et al., *European Journal of Biochemistry*, 269: 4202-4211, (2002)), presumably by breaking hydrogen bonds in the cellulose structure.

In spite of much research effort, there remains a need for an improved cellulase enzyme mixture for the hydrolysis of cellulose in a pretreated lignocellulosic feedstock. The absence of such an enzyme mixture represents a large hurdle in the commercialization of cellulose conversion to soluble sugars including glucose for the production of ethanol and other products.

SUMMARY OF THE INVENTION

The present invention provides a cellulase enzyme mixture. The present invention also provides a process for the hydrolysis of a lignocellulosic feedstock using the cellulase enzyme mixture.

It is an object of the invention to provide an improved enzyme mixture for the enzymatic hydrolysis of a lignocellulosic feedstock.

The inventors have found that adjusting the ratios of accessory enzymes, namely EG4, Swollenin and Cip1, with respect to one another within a cellulase enzyme mixture can improve the hydrolysis of pretreated lignocellulosic feedstocks. For example, it has been found that the inclusion of EG4 in a cellulase enzyme mixture at a fractional concentration (w/w for each of EG4, Swollenin and Cip1 as a function of the total amount of EG4, Swollenin and Cip1 in the cellulase enzyme mixture) of about 0.25 to about 0.83., Swollenin at a fractional concentration of about 0 to about 0.66 and Cip1 at a fractional concentration of 0 to about 0.33 measured relative to EG4, Swollenin and Cip1 enzymes present in the enzyme mixture can significantly improve the hydrolysis of a pretreated feedstock in relation to a corresponding wild-type enzyme composition. Previous work has not tested varying ratios of such accessory components in combination in the hydrolysis of pretreated lignocellulosic feedstock, but rather has focused on improving enzyme activity by modulating the levels of individual cellulase components.

Thus, according to a first aspect of the invention, there is provided an isolated cellulase enzyme mixture for hydrolyzing a pretreated lignocellulosic feedstock to soluble sugars which comprises primary cellulase mixture comprising CBH1, CBH2, EG1 and EG2 and an accessory enzyme mixture comprising EG4 at a fractional concentration ($f_{EG4}$) of about 0.09 to about 0.91 (w/w), for example of about 0.25 to about 0.83 (w/w); Swollenin at a fractional concentration ($f_{Swo1}$) of about 0.09 to about 0.91 (w/w), for example of about 0 to about 0.66; and Cip1 at a fractional concentration ($f_{Cip1}$) of 0 to about 0.42 (w/w), for example of about 0 to about 0.33, which fractional concentrations are measured relative to the total weight of the EG4, Swollenin and Cip1 enzymes present in the cellulase enzyme mixture.

According to a second aspect of the invention, there is provided a process for converting a pretreated lignocellulosic feedstock to soluble sugars comprising enzymatically hydrolyzing the pretreated lignocellulosic feedstock with the cellulase enzyme mixture as defined above.

According to a third aspect of the invention, there is provided a method ve for hydrolyzing a pretreated lignocellulosic feedstock to soluble sugars using the cellulase mixture as defined above.

According to embodiments of each aspect of the invention, the enzyme mixture comprises CBH1, CBH2, EG1 and EG2 primary cellulase enzymes. The primary cellulase enzymes may have a combined content of about 70 to about 95 wt % and the accessory enzymes may have a combined content of about 5 to about 30 wt % measured relative to the total weight percent of the primary cellulase enzymes and accessory enzymes present in the enzyme mixture. The primary cellulase enzymes may have a combined content of about 70 to about 90 wt % and the accessory enzymes have a combined content of about 10 to about 30 wt % measured relative to the total weight percent of the primary cellulase enzymes and accessory enzymes present in said enzyme mixture.

In embodiments of any of the foregoing aspects of the invention, the primary and accessory enzymes have a combined content of about 70 to about 100 wt % measured relative to the total protein present in the enzyme mixture.

The CBH1 and CBH2 enzymes may have a combined content of about 55 to about 85 wt % and the EG1 and EG2 enzymes may have a combined content of about 15 to about 45 wt % measured relative to the total combined weight of the CBH1, CBH2, EG1 and EG2 enzymes present in the cellulase enzyme mixture. In one embodiment of the invention, the CBH1 and CBH2 enzymes may each be present at a fractional concentration of about 0.25 to about 0.75 (w/w) measured relative to the combined total weight of CBH1 and CBH2 enzymes present in the cellulase enzyme mixture. In another embodiment of the invention, the EG1 and EG2 enzymes may each be present at respective fractional concentrations of about 0.35 to about 0.95 (w/w) and about 0.05 to about 0.65 (w/w) measured relative to the combined total weight of EG1 and EG2 enzymes present in the cellulase enzyme mixture.

The EG4 enzyme is present at a fractional concentration of about 0.33 to about 0.50, the Swollenin enzyme is present at a fractional concentration of about 0.33 to about 0.58 and the Cip1 is present at a fractional concentration of about 0.08 to about 0.25 relative to the total weight of the EG4, Swollenin and Cip1 enzymes present in the celllulase enzyme mixture.

The primary and accessory enzymes may be expressed from coding sequences from a fungal source. The fungal source can be an *Ascomycete* or *Basidomycete* fungus. The fungal source is selected from *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Fusarium* ssp., *Penicillium* ssp., *Magnaporthe* ssp., and *Phanerochaete* ssp. The fungal source may be a *Trichoderma* ssp.

The primary and accessory enzymes may be produced by expression in an endogenous organism from which the primary and accessory enzymes are derived. Alternatively, the primary and accessory enzymes may be produced by expression in a heterologous organism. Preferably the primary and accessory enzymes are produced by expression in *Trichoderma reesei*.

The cellulase enzyme mixture may be a blend of secreted enzymes from a microbial source. According to this embodiment, the primary and accessory enzymes make up between about 70 and about 100 wt % of the secreted enzymes in the blend and additional non-cellulase enzymes make up between 0 and about 30 wt % of the total secreted enzymes in the blend. The additional non-cellulase enzymes secreted in the blend may include β-glucosidase.

According to another aspect of the invention, there is provided a cellulase enzyme mixture for hydrolyzing a pretreated lignocellulosic feedstock to soluble sugars that comprises a primary enzyme mixture comprising CBH1, CBH2, EG1 and EG2 and an accessory enzyme mixture comprising EG4, Swollenin and Cip1 accessory enzymes, each of th EG4, Swollenin and Cip1 accessory enzymes being present at a fractional concentration ($f_{EG4}$, $f_{Swo1}$ and $f_{Cip1}$) measured relative to all accessory enzymes present in the cellulase enzyme mixture that provides an improvement in activity on a pretreated lignocellulosic feedstock of at least about 10% relative to a native enzyme mixture secreted by *Trichoderma reesei* wild-type defined herein as a Benchmark Blend.

DETAILED DESCRIPTION OF THE INVENTION

Figure 1:
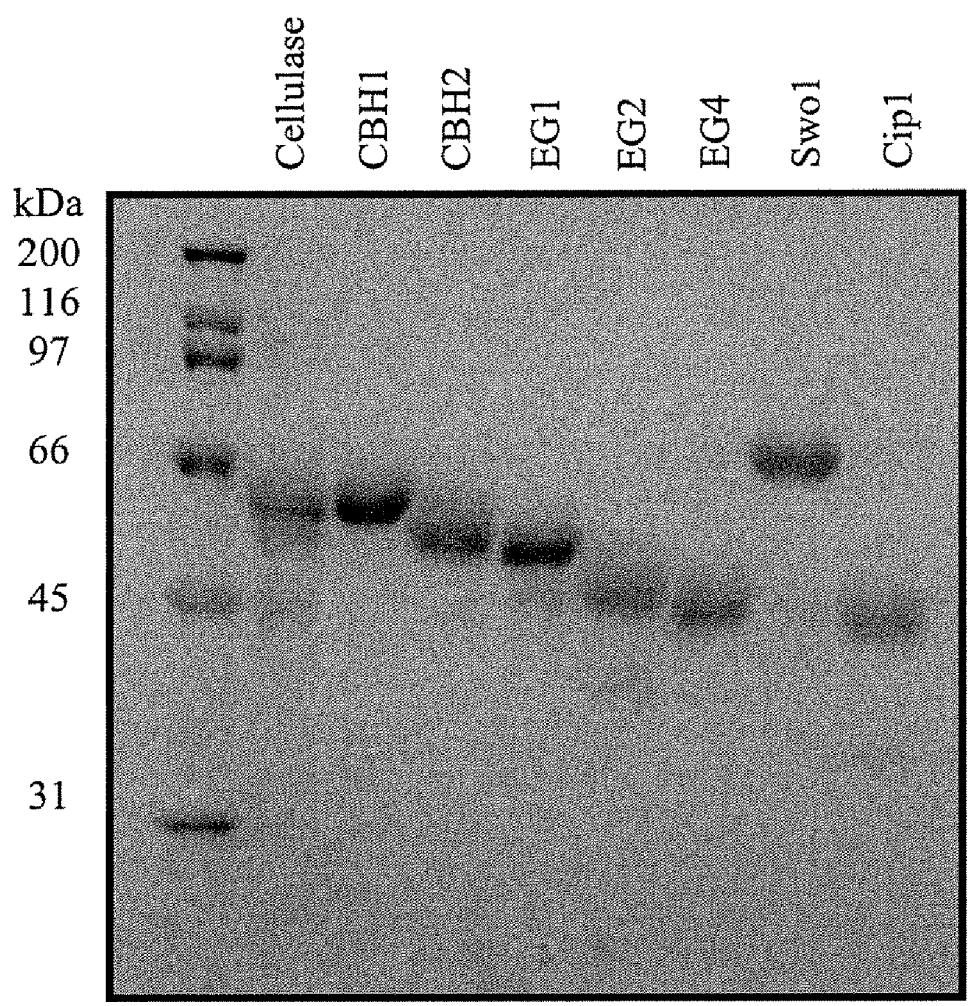
FIG. 1 shows of an SDS-PAGE gel of purified primary and accessory components after visualization with Coomassie Blue stain. A commercial *Trichoderma* cellulase and molecular mass standards are shown for reference. Densitometry analysis of this gel indicated that the purified components were substantially pure. CBH1 and CBH2 preparations were of a purity >95%. EG1, EG2, EG4, Swo1 and Cip1 were of a purity >90%.

The present invention provides a cellulase enzyme mixture. The present invention also provides a process for the hydrolysis of a lignocellulosic feedstock using the cellulase enzyme mixture.

The following description is of preferred embodiments.

The present invention relates to a cellulase enzyme mixture comprising primary cellulases and accessory enzymes to be used for hydrolyzing a pretreated lignocellulosic feedstock. "Accessory enzymes" or "accessory components" are defined herein as the endoglucanase, EG4, Swollenin (Swo1) and Cip1. "Primary cellulase enzymes", "primary cellulases", "primary components" or "PC" are defined herein as the cellobiohydrolases, CBH1 and CBH2, and the endoglucanases, EG1 and EG2. In addition to the primary cellulases, CBH1, CBH2, EG1 and EG2, and the accessory enzymes, EG4, Swollenin and Cip1, the cellulase enzyme mixture may comprise additional enzymes including other cellobiohydrolases or endoglucanases and hemicellulases, as well as β-glucosidase enzyme components as described in further detail herein.

The following definitions refer to classification of cellobiohydrolases, endoglucanases and β-glucosidases as defined by the by the Joint Commission on Biochemical Nomenclature of the International Union of Biochemistry and Molecular Biology (Published in *Enzyme Nomenclature* 1992, Academic Press, San Diego, Calif., ISBN 0-12-227164-5; with supplements in *Eur. J. Biochem.* 1994, 223, 1-5; *Eur. J. Biochem.* 1995, 232, 1-6; *Eur. J. Biochem.* 1996, 237, 1-5; *Eur. J. Biochem.* 1997, 250; 1-6, *and Eur. J. Biochem.* 1999, 264, 610-650, each of which are incorporated herein by reference; also see: chem.qmul.ac.uk/iubmb/enzyme/) and to the glycohydrolase families of cellulases and β-glucosidases as defined by the CAZy system which is accepted as a standard nomenclature for glycohydrolase enzymes (Coutinho, P. M. & Henrissat, B., 1999, "Carbohydrate-active enzymes: an integrated database approach." *In Recent Advances in Carbohydrate Bioengineering*, H. J. Gilbert, G. Davies, B. Henrissat and B. Svensson eds., The Royal Society of Chemistry, Cambridge, pp. 3-12, which is incorporated herein by reference; also see: afmb.cnrs-mrs.fr/CAZY/) and is familiar to those skilled in the art.

"EG4" is a carbohydrate active enzyme expressed from a nucleic acid sequence coding for a glycohydrolase (GH) Family 61 catalytic domain classified under EC 3.2.1.4 or any protein, polypeptide or fragment thereof with 40% to 100%, or more preferably 50% to 100% amino acid sequence identity to the highly conserved sequence from amino acid 144 to amino acid 163 of the EG4 enzyme of *Trichoderma reesei* (GenPept accession No. CAA71999 and annotated as *Hypocrea jecorina* endoglucanase IV). For example, the EG4 enzyme may be obtained or derived from any one of the organisms listed in Table 1 which demonstrates at least 40% identity to the *Trichoderma reesei* EG4. The EG4 may be functionally linked to a carbohydrate binding module (CBM) with a high affinity for crystalline cellulose, such as a Family 1 cellulose binding domain.

TABLE 1

Sequence Identity of EG4 Enzymes to *Trichoderma reesei* EG4

| Organism | Protein | GenPept Accession | % Identity with *T. reesei* EG4 (aa 144-163) |
|---|---|---|---|
| *Neurospora crassa* | Endoglucanase IV (NCU07760.1) | EAA29018 | 80 |
| *Thielavia terrestris* | Cel61C | ACE10232 | 75 |
| *Gibberella zeae* | Cel61E | XP_383871 | 75 |
| *Thielavia terrestris* | Cel61D | ACE10233 | 70 |
| *Trichoderma reesei* | Cel61B | AAP57753 | 65 |
| *Phanerochaete chrysosporium* BKM-F-1767 | Cel61A | AAM22493 | 65 |
| *Thielavia terrestris* | Cel61B | ACE10231 | 60 |
| *Aspergillus kawachii* | Cel61A | BAB62318 | 52 |
| *Aspergillus nidulans* FGSC A4 | Endo-β1,4-glucanase (AN1602.2) | EAA64722 | 52 |
| *Thielavia terrestris* | Cel61E | ACE10234 | 50 |
| *Gibberella zeae* | Sequence 122805 from patent US 7214786 | ABT35335 | 45 |
| *Thielavia terrestris* | Cel61G | ACE10235 | 40 |

*For *T. reesei* EG4, amino acid 1 is the first amino acid of the secreted enzyme, such that the first eight amino acids are HGHINDIV.

"Swollenin" or "Swo1" is defined herein as any protein, polypeptide or fragment thereof with about 70% to 100% amino acid sequence identity, or more preferably about 75% to about 100% amino acid sequence identity, to amino acids 92-475 (comprising the expansin-like domain and its associated CBM, but lacking the Family 1 CBM and linker peptide) of the *Trichoderma reesei* Swollenin enzyme (GenPept Accession No. CAB92328, annotated as *Hypocrea jecorina* Swollenin). For example, the Swollenin enzyme may be obtained or derived from any one of the organisms listed in Table 2 which demonstrates at least about 70% identity to the Swollenin enzyme from *Trichoderma reesei*. Preferably, the Swollenin is functionally linked to a carbohydrate binding module (CBM) with a high affinity for crystalline cellulose, such as a Family 1 cellulose binding domain.

TABLE 2

Sequence Identity of Swollenin Enzymes to *Trichoderma reesei* Swollenin

| Organism | Protein | GenPept Accession | % Identity with *T. reesei* Swollenin (aa 92-475)* |
|---|---|---|---|
| *Hypocrea pseudokoningii* | Swollenin | ABV57767 | 95.8 |
| *Trichoderma asperellum* | Swollenin | ACB05430 | 92.4 |
| *Neosartorya fischeri* NRRL 181 | Fungal Cellulose Binding Domain Protein | XP_001257521 | 74.0 |
| *Aspergillus fumigatus* Af293 | Swollenin | XP_747748 | 70.2 |

*For *T. reesei* Swollenin, amino acid 1 is the first amino acid of the secreted enzyme, such that the first eight amino acids are QQNCAALF.

"Cip1" is defined herein as any protein, polypeptide or fragment thereof with about 40% to about 100% amino acid sequence identity, or more preferably about 56% to about 100% amino acid sequence identity, to amino acids 1-212 comprising the catalytic domain of the *Trichoderma reesei* Cip1 enzyme (GenPept Accession No. AAP57751, annotated as *Hypocrea jecorina* Cip1). For example, the Cip1 enzyme may be derived from any one of the organisms listed in Table 3 which demonstrates at least about 40% identity to the *Trichoderma reesei* Cip1 enzyme. Preferably, the Cip1 is functionally linked to a carbohydrate binding module (CBM) with a high affinity for crystalline cellulose, such as a Family 1 cellulose binding domain.

TABLE 3

Sequence Identity of Cip1 Enzymes to *Trichoderma reesei* Cip1

| Organism | Protein | GenPept Accession | % Identity with *T. reesei* Cip1 (aa 1-212)* |
|---|---|---|---|
| *Pyrenophora tritici-repentis* Pt-1C-BFP | Cip1 | XP_001937765 | 56.9 |
| *Streptomyces coelicolor* A3(2) | Putative Secreted Hydrolase | CAA18323 | 39.6 |
| *Herpetosiphon aurantiacus* ATCC 23779 | Cellulose-Binding Family II Protein | YP_001545140 | 38.8 |

*For *T. reesei* Cip1, amino acid 1 is the first amino acid of the secreted enzyme, such that the first eight amino acids are QISDDFES . . .

"CBH1" is a carbohydrate active enzyme expressed from a nucleic acid sequence coding for a glycohydrolase (GH) Family 7 catalytic domain classified under EC 3.2.1.91 or any protein, polypeptide or fragment thereof with about 60% to about 100% amino acid sequence identity, or more preferably about 65% to about 100% amino acid sequence identity, to the catalytic domain (amino acids 1-437) of the *Trichoderma* CBH1 enzyme (GenPept Accession No. CAH10320, annotated as *Hypocrea jecorina* CBH1). For example, the CBH1 enzyme may be derived from any one of the organisms listed in Table 4 which demonstrates at least 60% identity to the *Trichoderma reesei* CBH1 enzyme. The CBH1 may be functionally linked to a carbohydrate binding module (CBM) with a high affinity for crystalline cellulose, such as a Family 1 cellulose binding domain.

"CBH2" is defined as a carbohydrate active enzyme expressed from a nucleic sequence coding for a glycohydrolase (GH) Family 6 catalytic domain classified under EC 3.2.1.91 or any protein, polypeptide or fragment thereof with about 45% to about 100% amino acid sequence identity, or more preferably about 60% to about 100% amino acid sequence identity, to amino acids 83-447 comprising the catalytic domain of the *Trichoderma* CBH2 enzyme (GenPept Accesssion No. AAA34210, annotated as *Hypocrea jecorina* cellobiohydrolase II). For example, the CBH2 enzyme may be obtained or derived from any one of the organisms listed in Table 5 which demonstrates at least about 45% identity to the *Trichoderma reesei* CBH2 enzyme. The CBH2 may be functionally linked to a carbohydrate binding module (CBM) with a high affinity for crystalline cellulase, such as a Family 1 cellulose binding domain.

TABLE 4

Sequence Identity of CBH1 Enzymes to *Trichoderma reesei* CBH1

| Organism | Protein | GenPept Accession | % Identity with *T. reesei* CBH1 (1-437)* |
| --- | --- | --- | --- |
| *Hypocrea koningii* G-39 | Cellobiohydrolase (Cbh1) - Cel7A | CAA49596 | 100.0 |
| *Trichoderma viride* AS 3.3711 | Cellobiohydrolase I | AAQ76092 | 99.3 |
| *Trichoderma viride* | 1,4-beta-D-glucan Cellobiohydrolase | CAA37878 | 96.1 |
| *Trichoderma harzianum* | Cellobiohydrolase | AAF36391 | 81.9 |
| *Aspergillus niger* CBS 513.88 | 1,4-beta-D-glucan cellobiohydrolase A precursor | AAF04491 | 65.5 |
| *Talaromyces emersonii* | Cellobiohydrolase 1-Cel7A | AAL33603 | 65.0 |
| *Thermoascus aurantiacus* var. *levisporus* | Cellobiohydrolase Precursor | AAW27920 | 64.6 |
| *Aspergillus oryzae* KBN616 | Cellobiohydrolase C | BAC07255 | 63.8 |
| *Thermoascus aurantiacus* | Cellobiohydrolase Precursor | AAL16941 | 63.2 |
| *Penicillium occitanis* | Cellobiohydrolase I | AAT99321 | 63.2 |
| *Penicillium funiculosum* | xylanase/cellobiohydrolase | CAC85737 | 63.0 |
| *Cryphonectria parasitica* EP155 | Cellobiohydrolase | AAB00479 | 62.6 |
| *Acremonium thermophilum* ALKO4245 | Cellulose 1,4-beta-cellobiosidase | CAM98445 | 62.5 |
| *Aspergillus niger* CBS 513.88 | 1,4-beta-D-glucan cellobiohydrolase B precursor | AAF04492 | 61.8 |
| *Neurospora crassa* OR74A | Exoglucanase 1 Precursor | EAA33262 | 61.0 |
| *Penicillium chrysogenum* FS010 | Exo-cellobiohydrolase | AAV65115 | 60.8 |
| *Aspergillus oryzae* RIB 40 | Cellobiohydrolase D | BAE61042 | 60.4 |

*For *T. reesei* CBH1, amino acid 1 is the first amino acid of the secreted enzyme, such that the first eight amino acids are QSACTLQS . . .

TABLE 5

Sequence Identity of CBH2 Enzymes to *Trichoderma reesei* CBH2

| Organism | Protein | GenPept Accession | % Identity with *T. reesei* CBH2 (aa 83-447) |
| --- | --- | --- | --- |
| *Hypocrea koningii* | cellobiohydrolase II (Cbh2) | AAK01367.1 | 98.9 |
| *Trichoderma viride* CICC 13038 | cellobiohydrolase II (CbhII; Cbh2) | AAQ76094.1 | 98.9 |
| *Hypocrea koningii* 3.2774 | cellobiohydrolase II (Cbh2; CbhII) | ABF56208.1 | 98.1 |
| *Hypocrea koningii* AS3.2774 | cbh2 | ABG48766.1 | 97.8 |
| *Trichoderma parceramosum* | cellobiohydrolase II (CbhII) | AAU05379.2 | 97.8 |
| *Aspergillus nidulans* FGSC A4 | cellobiohydrolase (AN5282.2) | ABF50873.1 | 72.4 |
| *Aspergillus niger* CBS 513.88 | An12g02220 | CAK41068.1 | 72.4 |
| *Aspergillus oryzae* RIB 40 | AO090038000439 | BAE64227.1 | 67.8 |
| *Aspergillus niger* CBS 513.88 | An08g01760 | CAK39856.1 | 67.7 |

TABLE 5-continued

Sequence Identity of CBH2 Enzymes to *Trichoderma reesei* CBH2

| Organism | Protein | GenPept Accession | % Identity with *T. reesei* CBH2 (aa 83-447) |
|---|---|---|---|
| *Acremonium cellulolyticus* Y-94 | cellobiohydrolase II (Acc2) | AAE50824 | 67.3 |
| *Talaromyces emersonii* | cellobiohydrolase II (CbhII) | AAL78165.2 | 66.8 |
| *Gibberella zeae* K59 | Cel6 - Cel6 | AAQ72468.1 | 66.1 |
| *Fusarium oxysporum* | endoglucanase B | AAA65585.1 | 66.1 |
| *Neurospora crassa* OR74A | NCU09680.1 (64C2.180) | CAD70733.1 | 65.9 |
| *Aspergillus nidulans* FGSC A4 | AN1273.2 | EAA65866.1 | 65.5 |
| *Magnaporthe grisea* 70-15 | MG05520.4 | XP_360146.1 | 65.4 |
| *Chaetomium thermophilum* CT2 | cellobiohydrolase (Cbh2) | AAW64927.1 | 65.0 |
| *Humicola insolens* | avicelase 2 (Avi2) | BAB39154.1 | 63.7 |
| *Cochliobolus heterostrophus* C4 | cellobiohydrolase II (CEL7) | AAM76664.1 | 59.6 |
| *Agaricus bisporus* D649 | cellobiohydrolase II (Cel3; Cel3A) | AAA50607.1 | 57.7 |
| *Polyporus arcularius* 69B-8 | cellobiohydrolase II (Cel2) | BAF80327.1 | 57.1 |
| *Lentinula edodes* Stamets CS-2 | cellulase - Cel6B | AAK95564.1 | 56.3 |
| *Lentinula edodes* L54 | cellobiohydrolase (CbhII-1) | AAK28357.1 | 56.0 |
| *Malbranchea cinnamomea* | unnamed protein product | CAH05679.1 | 54.9 |
| *Phanerochaete chrysosporium* | cellobiohydrolase II | AAB32942.1 | 54.9 |
| *Volvariella volvacea* | cellobiohydrolase II-I (CbhII-I) | AAT64008.1 | 53.8 |
| *Chrysosporium lucknowense* | cellobiohydrolase (EG6; CBH II) - Cel6A | AAQ38151.1 | 49.5 |
| *Pleurotus sajor-caju* | cellobiohydrolase II | AAL15037.1 | 47.2 |
| *Trametes versicolor* | ORF | AAF35251.1 | 47.0 |
| *Neurospora crassa* OR74A | NCU03996.1 | XP_323315.1 | 46.8 |
| *Magnaporthe grisea* 70-15 | MG04499.4 | XP_362054.1 | 45.1 |

*For *T. reesei* CBH1, amino acid 1 is the first amino acid of the secreted enzyme, such that the first eight amino acids are QAACSSVWG.

"EG1" is defined as a carbohydrate active enzyme expressed from a nucleic acid sequence coding for a glycohydrolase (GH) Family 7 catalytic domain classified under EC 3.2.1.4 or any protein, polypeptide or fragment thereof with about 40% to about 100% amino acid sequence identity, or more preferably about 48% to about 100% amino acid sequence identity, to amino acids 1-374 comprising the catalytic domain of the *Trichoderma reesei* EG1 enzyme (GenPept Accession No. AAA34212, annotated as *Hyprocrea jecorina* endoglucanase I). For example, the EG1 enzyme may be obtained or derived from any one of the organisms listed in Table 6 which demonstrates at least about 40% identity to the *Trichoderma reesei* EG1 enzyme. The EG1 is functionally linked to a carbohydrate binding module (CBM) with a high affinity for crystalline cellulase, such as a Family 1 cellulose binding domain.

"EG2" is defined as a carbohydrate active enzyme expressed from a nucleic acid sequence coding for a glycohydrolase (GH) Family 5 catalytic domain classified under EC 3.2.1.4 or any protein, polypeptide or fragment thereof with about 40% to about 100% amino acid sequence identity, or more preferably about 48% to about 100% amino acid sequence identity, to the amino acids 202 to 222 of the *Trichoderma* EG2 enzyme (GenPept Accession No. AAA34213, annotated as *Hypocrea jecorina* endoglucanase III). The highly conserved region represented by amino acids 202-222 of the *Trichoderma reesei* EG2 amino acid sequence includes one of the two catalytic glutamic acid residues that characterize GH Family 5. For example, the EG2 enzyme may be obtained or derived from any one of the organisms listed in Table 7 which demonstrates at least about 40% identity to the *Trichoderma reesei* EG2 enzyme. The EG2 may be functionally linked to a carbohydrate binding module (CBM) with a high affinity for crystalline cellulase, such as a Family 1 cellulose binding domain.

TABLE 6

Sequence Identity of EG1 Enzymes to *Trichoderma reesei* EG1

| Organism | Protein | GenPept Accession | % Identity with *T. reesei* EG1 (aa 1-374)* |
|---|---|---|---|
| *Trichoderma viride* AS 3.3711 | Endoglucanase I | AAQ21382 | 99.5 |
| *Trichoderma longibrachiatum* | Endo-1,4-glucanase I | CAA43059 | 95.5 |
| *Hypocrea pseudokoningii* | Endoglucanase I | ABM90986 | 95.2 |
| *Penicillium decumbens* 114-2 | Endoglucanase I | ABY56790 | 62.5 |
| *Aspergillus oryzae* RIB 40 | Endo-1,4-glucanase | BAE66197 | 49.1 |
| *Aspergillus oryzae* KBN616 | Endo-1,4-glucanase (CelB) | BAA22589 | 48.9 |
| *Neurospora crassa* OR74A | Endoglucanase EG-1 precursor | EAA27195 | 48.7 |
| *Aspergillus nidulans* FGSC A4 | Endo-β-1,4-glucanase | EAA63386 | 47.9 |
| *Neurospora crassa* OR74A | Hypothetical Protein | XP_324211 | 41.7 |

*For *T. reesei* EG1, amino acid 1 is the first amino acid of the secreted enzyme, such that the first eight amino acids are QQPGTSTP.

TABLE 7

Sequence Identity of EG2 Enzymes to *Trichoderma reesei* EG2

| Organism | Protein | GenPept Accession | % Identity with *T. reesei* EG2 (aa 202-222)* |
|---|---|---|---|
| *Trichoderma viride* | Endoglucanase | ABQ95572 | 100 |
| *Trichoderma viride* AS 3.3711 | Endoglucanase III | AAQ21383 | 100 |
| *Trichoderma viride* MC300-1 | Endo-1,4-glucanase II | BAA36216 | 100 |
| *Trichoderma* sp. C-4 | Endo-1,4-glucanase | AAR29981 | 92 |
| *Phanerochaete chrysosporium* | Endoglucanase - Cel5A | AAU12275 | 72 |
| *Macrophomina phaseolina* | Endo-1,4-glucanase | AAB03889 | 64 |
| *Cryptococcus* sp. S-2 | Carboxymethylcellulase | ABP02069 | 56 |
| *Cryptococcus flavus* | Carboxymethylcellulase | AAC60541 | 50 |
| *Irpex lacteus* MC-2 | Endoglucanase | BAD67544 | 48 |
| *Hypocrea jecorina* QM6a | Cel5B | AAP57754 | 48 |
| *Macrophomina phaseolina* | Endo-1,4-glucanase | AAB51451 | 44 |
| *Thermoascus aurantiacus* IFO 9748 | EGI Precursor | AAL16412 | 44 |
| *Trametes hirsuta* | Endoglucanase | BAD01163 | 44 |
| *Aspergillis oryzae* | Endo-1,4-glucanase (CelE) | BAD72778 | 44 |
| *Talaromyces emersonii* | Endo-1,4-glucanase | AAL33630 | 40 |
| *Humicola grisea* var. *thermoidea* IFO9854 | Cellulase (Endo-1,4-glucanase 3) | BAA12676 | 40 |
| *Humicola insolens* | Endo-1,4-glucanase IV | CAA53631 | 40 |
| *Aspergillis kawachi* | Endoglucanase C (Cel5B) | BAB62319 | 40 |
| *Aspergillis nidulans* | Endo-β-1,4-glucanase | ABF50848 | 40 |

*For *T. reesei* EG2, amino acid 1 is the first amino acid of the secreted enzyme, such that the first eight amino acids are QQTVWGQC.

"β-Glucosidase" is defined as any enzyme from the GH Family 3 or GH Family 1 that is also classified under EC 3.2.1.21 or any protein, peptide or fragment thereof. The β-glucosidase may be of fungal origin. For example, the β-Glucosidase may be from a species of *Trichoderma*, *Hypocrea* or *Aspergillus*, or the β-Glucosidase may be from *Trichoderma reesei*.

Sequence identity can be readily determined by alignment of the amino acids of the two sequences, either using manual alignment, or any sequence alignment algorithm as known to one of skill in the art, for example but not limited to, BLAST algorithm (BLAST and BLAST 2.0; Altschul et al., Nuc. Acids Res. 25:3389-3402, 1977; and Altschul et al., J. Mol. Biol. 215:403-410, 1990), the algorithm disclosed by Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)). In the case of conducting BLAST alignments and sequence identity determinations for cellulase enzymes, only the amino acid sequences comprising the catalytic domains are considered.

Ratios of the accessory components, namely EG4, Swollenin and Cip1, exhibiting a particular advantage in carrying out the hydrolysis of a lignocellulosic feedstock have been identified. These sets of mixtures are defined herein by the fractional concentration—i.e., the weight of each individual accessory enzyme as a function of the total combined weight of all accessory enzymes present in the cellulase enzyme mixture. The fraction of EG4 relative to EG4, Swo1 and Cip1 is referred to herein as $f_{EG4}$ where:

$$f_{EG4} = EG4/(EG4+Swo1+Cip1).$$

The Swo1 fraction relative to the EG4, Swo1 and Cip1 is referred to herein as $f_{Swo1}$ where:

$$f_{Swo1} = Swo1/(EG4+Swo1+Cip1).$$

The Cip1 fraction relative to the EG4, Swo1 and Cip1 is referred to herein as $f_{Cip1}$ where:

$$f_{Cip1} = Cip1/(EG4+Swo1+Cip1).$$

Figure 4:
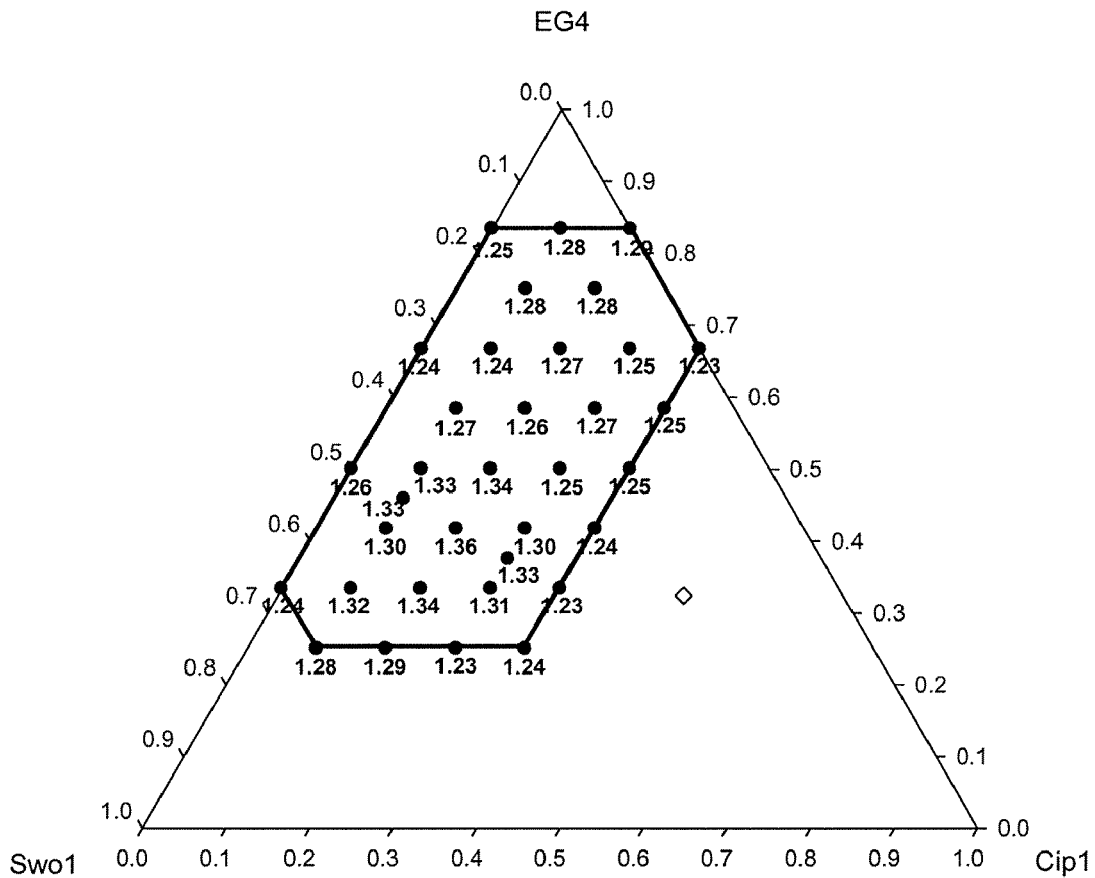
FIG. 4 shows accessory component blends with significantly higher activity than the Benchmark Blend (1.16). The activities of these blends are greater than or equal to 1.23. This region of ternary blend space we refer to herein as Zone 1.
Figure 5:
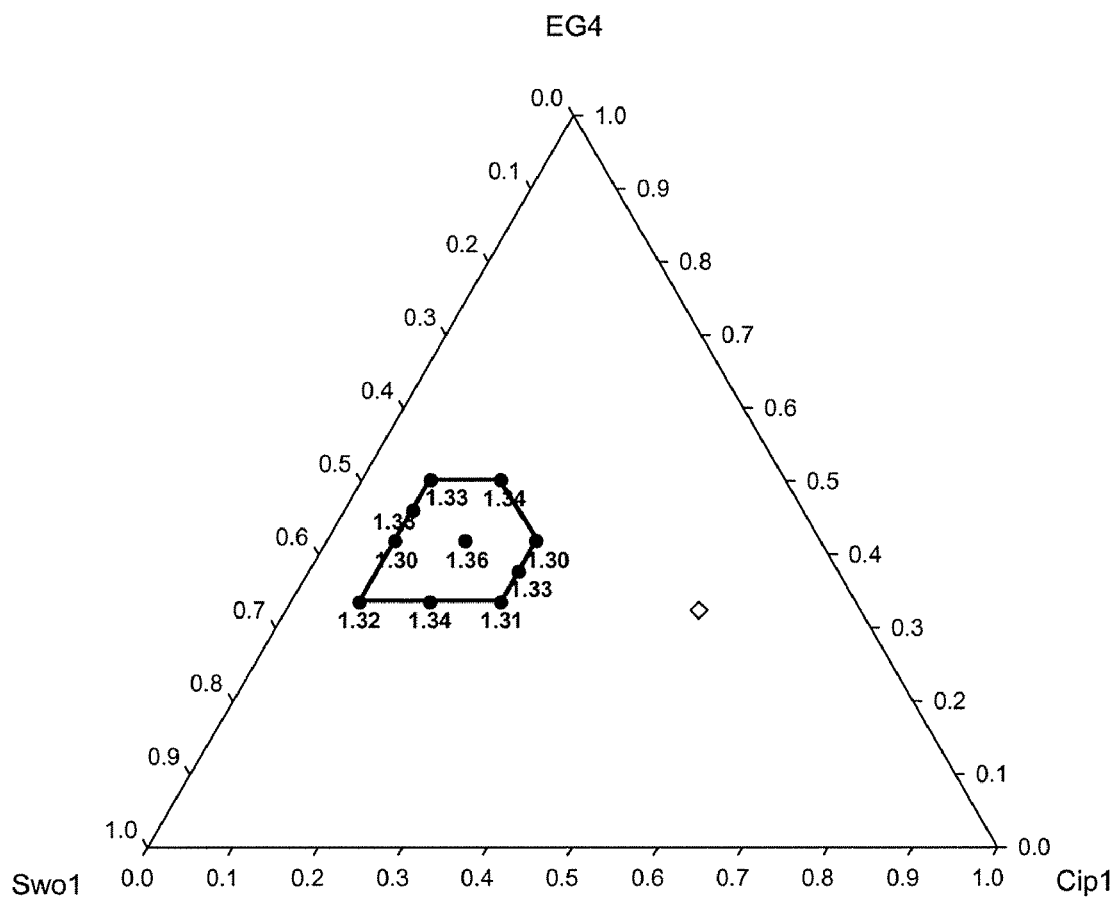
FIG. 5 shows accessory component blends with the highest activity. The activities of these blends are greater than or equal to 1.30. This region of ternary blend space we refer to herein as Zone 2.

As shown in FIGS. 4 and 5, in a cellulase mixture comprising primary cellulases and accessory enzymes, when the fraction of EG4 is between about 0.25 and about 0.83 ($f_{EG4}$), the fraction of Swo1 is between about 0 and about 0.66 ($f_{Swo1}$) and the fraction of Cip1 is between 0 and 0.33 ($f_{Cip1}$) significantly higher levels of hydrolysis have been observed relative to a commercial *Trichoderma* cellulase mixture referred to herein as a "Benchmark Blend". This mixture of accessory enzymes covers Zone 1 as outlined in FIG. 4. Preferably, the $f_{EG4}$ is between about 0.33 and about 0.50, the $f_{Swo1}$ is between about 0.33 and about 0.58 and the $f_{Cip1}$ is between about 0.08 and about 0.25. This mixture of accessory enzymes covers Zone 2 as outlined in FIG. 5.

Thus, according to the present invention, the EG4 enzyme is present at a fractional concentration of about 0.25 to about 0.83 ($f_{EG4}$), or any value therebetween, for example 0.25, 0.30, 0.35, 0.40, 0.45, 0.50, 0.55, 0.60, 0.65, 0.70, 0.75, 0.80, 0.83, or any value therebetween. Preferably, the EG4 fractional concentration ($f_{EG4}$) is about 0.33 to about 0.50, or any value therebetween, for example, 0.33, 0.34, 0.36, 0.38, 0.40, 0.42, 0.44, 0.46, 0.48, 0.50 or any value therebetween. The Swollenin enzyme is present at a fractional concentrations of about 0 to about 0.66 ($f_{Swo1}$), or any value therebetween, for example 0, 0.05, 0.10, 0.15, 0.20, 0.25, 0.30, 0.35, 0.40, 0.45, 0.50, 0.55, 0.60, 0.65, 0.66 or any value therebetween. Preferably, the Swollenin fractional concentration ($f_{Swo1}$) is about 0.33 to about 0.58, or any value therebetween, for example 0.33, 0.34, 0.36, 0.38, 0.40, 0.42, 0.44, 0.46, 0.48, 0.50, 0.52, 0.54, 0.56, 0.58, or any value therebetween. Cip1 is present at a fractional concentration of 0 to 0.33 ($f_{Cip1}$), or any value therebetween, for example 0, 0.05, 0.10, 0.15, 0.20, 0.25, 0.30, 0.33 or any value therebetween. Preferably, Cip1 is at a fractional concentration of 0.08 to 0.25, or any value therebetween, for example 0.08, 0.10, 0.12, 0.14, 0.16, 0.18, 0.20, 0.22, 0.24, 0.25 or any value therebetween.

The combined contents of the accessory components (EG4, Swo1 and Cip1) may be between about 5 wt % and about 30 wt % or any wt % therebetween, for example between about 10 wt % and about 30 wt % or any wt % therebetween, and the primary cellulase enzymes may be between about 70 wt % and 95 wt %, or any wt % therebetween, for example between about 10 wt % and about 70 wt %, or any wt % therebetween, measured relative to both the accessory and primary cellulase enzymes in the enzyme mixture. For example, the accessory components may be present at about 5, 6, 7, 8, 9, 10, 11, 12, 13, 14, 15, 16, 17, 18, 19, 20, 21, 22, 23, 24, 25, 26, 27, 28, 29, 30 or 30.5 wt % relative to the combined weight of all accessory and primary cellulase enzymes present in the enzyme mixture. The primary cellulase enzymes may be present at about 69.5, 70, 71, 7, 73, 74, 75, 76, 77, 78, 79, 80, 81, 82, 83, 84, 85, 86, 87, 88, 89, 90, 91, 92, 93, 94, 94.5 or 95 wt % relative to the combined weight of all accessory and primary cellulase enzymes present in the enzyme mixture.

The ratio of the primary cellulase components, CBH1, CBH2, EG1 and EG2, with respect to one another may be adjusted as desired to achieve further improvements in hydrolysis. Ratios of primary cellulases in the enzyme mixture that may be employed in the practice of the invention are as disclosed in co-pending U.S. Application No. 2008/0057541A1 (which is incorporated herein by reference). Examples which should not be considered limiting are provided below. However, it should be appreciated that the invention is not limited in any manner by the specific ratios of primary cellulases described therein.

For example, the cellobiohydrolases CBH1 and CBH2 within the cellulase enzyme mixture of the present invention (i.e., the combined content of CBH1 and CBH2) may be present at greater than or equal to 55 wt % and less than 85 wt %, or any wt % therebetween, of the primary cellulase mixture composed of CBH1, CBH2, EG1 and EG2, for example CBH1 and CBH2 may be present at 55, 60, 65, 70, 75, 80, 85 wt % or any wt % therebetween. The endoglucanases, EG1 and EG2, within the cellulase enzyme mixture of the present invention may be present at greater than or equal to 15% and less than 45% wt %, or any wt % therebetween, of the primary cellulase mixture composed of CBH1, CBH2, EG1 and EG2, for example EG1 and EG2 may be present at 15, 16, 18, 20, 22, 24, 25,30, 35, 40, 45 wt % or any wt % therebetween.

In further preferred embodiments of the invention, the CBH1 and CBH2 enzymes are each present at respective fractional concentrations of 0.25 to 0.75 (w/w) or any value therebetween and 0.25 to 0.75 (w/w) or any value therebetween measured relative to the combined content of CBH1 and CBH2 enzymes present in the enzyme mixture. For example, the CBH1 and CBH2 may each be present at fractional concentration of 0.25, 0.30, 0.35, 0.40, 0.45,0.50, 0.55, 0.60, 0.65, 0.70, 0.75 or any value therebetween. The EG1 and EG2 enzymes are each present at respective fractional concentrations of 0.35 to 0.95 (w/w) or any value therebetween and 0.05 to 0.65 (w/w) or any value therebetween measured relative to the combined content of EG1 and EG2 enzymes present in the enzyme mixture. For example, the EG1 may be present at a fractional concentration of 0.35, 0.40, 0.45, 0.50,0.55, 0.60, 0.65, 0.70, 0.75, 0.80, 0.85, 0.90, 0.95 or any value therebetween, and the EG2 may be present at a fractional concentration of 0.05, 0.10, 0.15, 0.20, 0.25, 0.30, 0.35, 0.40, 0.45, 0.50, 0.55, 0.60, 0.65 or any value therebetween.

The cellulase enzyme mixture of the invention is used for the enzymatic hydrolysis of a "pretreated lignocellulosic feedstock." A pretreated lignocellulosic feedstock is a material of plant origin that, prior to pretreatment, contains at least 20% cellulose (dry wt), more preferably greater than about 30% cellulose, even more preferably greater than 40% cellulose, for example 20, 22, 24, 26, 28, 30, 32, 34, 36, 38, 40, 42, 44, 46, 48, 50, 55, 60, 65, 70, 75, 80, 85, 90% or any % therebetween, and at least 10% lignin (dry wt), more typically at least 12% (dry wt) and that has been subjected to physical and/or chemical processes to make the fiber more accessible and/or receptive to the actions of cellulolytic enzymes.

After pretreatment, the lignocellulosic feedstock may contain higher levels of cellulose. For example, if acid pretreatment is employed, the hemicellulose component is hydrolyzed, which increases the relative level of cellulose. In this case, the pretreated feedstock may contain greater than about 20% cellulose and greater than about 12% lignin. In one embodiment, the pretreated lignocellulosic feedstock contains greater than about 20% cellulose and greater than about 10% lignin.

Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; grasses such as switch grass, miscanthus, cord grass, and reed canary grass; or post-consumer waste paper products.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, 4,600,590, Weil et al. (1997) and Ohgren, K., et al. (2005); which are incorporated herein by reference).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, or sulfuric acid. For example, the acid used during pretreatment is sulfuric acid.

One method of performing acid pretreatment of the feedstock is steam explosion using the process conditions set out in U.S. Pat. No. 4,461,648 (Foody, which is herein incorporated by reference). Another method of pretreating the feedstock slurry involves continuous pretreatment, meaning that the lignocellulosic feedstock is pumped through a reactor continuously. Continuous acid pretreatment is familiar to those skilled in the art; see, for example, U.S. Pat. No. 5,536, 325 (Brink); WO 2006/128304 (Foody and Tolan); and U.S. Pat. No. 4,237,226 (Grethlein), which are each incorporated herein by reference. Additional techniques known in the art may be used as required such as the process disclosed in U.S. Pat. No. 4,556,430 (Converse et al.; which is incorporated herein by reference).

As noted above, the pretreatment may be conducted with alkali. In contrast to acid pretreatment, pretreatment with alkali does not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

An example of a suitable alkali pretreatment is Ammonia Freeze Explosion, Ammonia Fiber Explosion or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

The pretreated lignocellulosic feedstock may be processed after pretreatment but prior to the enzymatic hydrolysis by any of several steps, such as dilution with water, washing with water, buffering, filtration, or centrifugation, or a combination of these processes, prior to enzymatic hydrolysis, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars include, but are not limited to, glucose, cellobiose, cellodextrins, or mixtures thereof. The soluble sugars may be predominantly cellobiose and glucose. The soluble sugars may predominantly be glucose.

The enzymatic hydrolysis process preferably converts about 80% to about 100% of the cellulose to soluble sugars, or any range therebetween. More preferably, the enzymatic hydrolysis process converts about 90% to about 100% of the cellulose to soluble sugars, or any range therebetween. In the most preferred embodiment, the enzymatic hydrolysis process converts about 98% to about 100% of the cellulose to soluble sugars, or any range therebetween.

The enzymatic hydrolysis using the cellulase mixture may be batch hydrolysis, continuous hydrolysis, or a combination thereof. The hydrolysis may be agitated, unmixed, or a combination thereof.

The enzymatic hydrolysis is preferably carried out at a temperature of about 45° C. to about 75° C., or any temperature therebetween, for example a temperature of 45, 50, 55, 60, 65, 70, 75° C., or any temperature therebetween, and a pH of about 3.5 to about 7.5, or any pH therebetween, for example a temperature of 3.5, 4.0, 4.5, 5.0, 5.5, 6.0, 6.5, 7.0, 7.5, or pH therebetween. The initial concentration of cellulose in the hydrolysis reactor, prior to the start of hydrolysis, is preferably about 4% (w/w) to about 15% (w/w), or any amount therebetween, for example 4, 6, 8, 10, 12, 14, 15% or any amount therebetween. The combined dosage of all primary cellulase enzymes may be about 1 to about 100 mg protein per gram cellulose, or any amount therebetween, for example 1, 5, 10, 15, 20, 25, 30, 40, 50, 60, 70, 80, 90, 100 mg protein per gram cellulose or any amount therebetween. The hydrolysis may be carried out for a time period of about 12 hours to about 200 hours, or any time therebetween, for example, the hydrolysis may be carried out for a period of 15 hours to 100 hours, or any time therebetween, or it may be carried out for 12, 14, 15, 20, 25, 30, 35, 40, 45, 50, 55, 60, 65, 70, 75, 80, 85, 90, 95, 100, 120, 140, 160, 180, 200 or any time therebetween. It should be appreciated that the reaction conditions are not meant to limit the invention in any manner and may be adjusted as desired by those of skill in the art.

The enzymatic hydrolysis is typically carried out in a hydrolysis reactor. The enzyme mixture is added to the pretreated lignocellulosic feedstock (also referred to as the "substrate") prior to, during, or after the addition of the substrate to the hydrolysis reactor.

Preferably, the enzyme mixture is produced in one or more submerged liquid culture fermentations and may be separated from the cells at the end of the fermentation by filtration, centrifugation, or other processes familiar to those skilled in the art. The cell-free cellulase-containing fraction may then be concentrated (for example, via ultrafiltration), preserved, and/or stabilized prior to use. Alternatively, the primary cellulases are not separated from the cells, but are added to the enzymatic hydrolysis with the cells.

The cellulase mixture may be an aqueous solution of protein in water, a slurry of protein in water, a solid powder or granule, or a gel. The blend comprising cellulase enzymes may include additives such as buffers, detergents, stabilizers, fillers, or other such additives familiar to those skilled in the art.

The enzyme mixture of the invention may be derived from any one of a number of sources. The coding sequences of the enzymes of the cellulase enzyme mixture are preferably from *Ascomycotina* or *Basidomycotina*. For example, the coding sequences are from the genera selected from *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomiun* ssp., *Fusarium* ssp., *Penicillium* ssp., *Magnaporthe* ssp., and *Phanerochaete* ssp. Preferably, the coding sequences for the primary cellulases and accessory enzymes are from *Trichoderma reesei*.

The primary cellulases and accessory enzymes of the invention may be cloned and expressed in any suitable microorganism known to those of skill in the art as an expression host, such as a bacterium or a fungus. Preferably, the microorganism is a fungus. The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g., U.S. Pat. No. 6,939,704).

All of the enzymes in the cellulase enzyme mixture may be secreted from one strain of an organism, referred to herein as a "complete blend" of secreted enzymes. By the term "complete blend", it is meant all proteins secreted extracellularly into the growth medium by a specific microorganism. In one embodiment of the invention, the primary and accessory enzymes make up between about 70 and about 100 wt % of the secreted enzymes in the blend, or any amount therebetween, for example 70, 75, 80, 85, 90, 95, 100%, or any amount therebetween. Preferably, the enzyme mixture is part of a secreted cellulase system that includes β-glucosidase.

The enzyme mixture may include the complete blend of enzymes secreted by *Trichoderma reesei*.

Alternatively, the enzyme mixture may be expressed individually or in sub-groups from different strains of different organisms and the enzymes combined to make the cellulase enzyme mixture. It is also contemplated that the enzyme mixture may be expressed individually or in sub-groups from different strains of a single organism, such as from different strains of *Trichoderma reesei* and the enzymes combined to make the cellulase enzyme mixture. Preferably, all of the enzymes may be expressed from a single strain of *Trichoderma reesei*.

The cellulase enzyme mixture may be expressed from fungal coding sequences. In this embodiment, the coding sequences would be from any fungal source. The terms "fungus," "fungi," "fungal," "*Ascomycotina*," "*Basidiomycotina*" and related terms (e.g. "ascomycete" and "basidiomycete") and are meant to include those organisms defined as such in *The Fungi: An Advanced Treatise* (G C Ainsworth, F K Sparrow, A S Sussman, eds.; Academic Press 1973).

The concentration of accessory enzymes relative to the primary cellulase enzymes within the enzyme mixture may be adjusted by deleting one or more of the nucleic acid sequences encoding for the primary cellulase enzymes or other secreted enzymes within the host cell according to known techniques, followed by determining the amounts of the remaining enzymes that are expressed. Deleting a nucleic acid sequence may be achieved by engineering a construct that includes sequences from the target nucleic acid sequence itself into the construct, but in altered form. After transformation of the construct into the expression host, recombination then occurs with the altered target nucleic acid sequence, resulting in the insertion of the altered sequence to disrupt the native nucleic acid sequence. With its sequence interrupted, the altered gene in most cases will be translated into a non-functional protein, or not translated at all. An example of a method that may be used to delete a target nucleic acid sequence from a host cell include, but are not limited to, methods describe in U.S. Pat. No. 5,298,405 which is incorporated herein by reference.

The concentration of accessory enzymes relative to the primary cellulase enzymes within the enzyme mixture may also be adjusted by adding one or more desired enzymes to the cellulase mixture that is produced by a host cell, including a host cell that has been modified to result in the disruption of one or more nucleic acids that encode for the primary cellulase enzymes as outlined above, and determining the concentration of each enzyme within the final cellulase enzyme mixture.

The ratio of the accessory components with respect to one another in a cellulase enzyme mixture may be adjusted in the enzyme mixture by genetic modification of an expression host. For example, the expression host may be genetically modified to adjust the expression of one or more accessory enzymes and optionally the primary cellulase enzymes as required by the introduction of an expression construct encoding an accessory enzyme according to known recombinant techniques. For example, this may be achieved by the introduction of multiple copies of a construct containing a nucleic acid sequence encoding the accessory enzyme to be expressed. A plasmid comprising the expression construct may contain sequences that allow it to recombine with sequences in the genome of the expression host so that it integrates into the host genome. Multiple copies of the nucleic acid sequence encoding the accessory enzyme to be expressed may be integrated into the genome of the host organism to increase levels of expression of the gene. Alternatively, the plasmid may remain in the host in non-integrated from, in which case it replicates independently from the host genome. In another embodiment, primary cellulases, accessory enzymes, or a combination thereof, may also be overexpressed by the introduction of a promoter upstream of a target native nucleic acid sequence that increases the level of expression of the native sequence over endogenous levels.

The expression levels of the accessory enzymes and primary cellulase enzymes may also be modulated by adjusting the pH of the fermentation. In one embodiment of the invention, the cellulase enzyme mixture is produced by conducting a fermentation at a pH of about 2 to about 5 to adjust the expression of the primary cellulase enzymes and the accessory enzymes. For example, the pH of the fermentation may be about 2.0, 2.2, 2.4, 2.6, 2.8, 3.0, 3.2, 3.4, 3.6, 3.8, 4.0, 4.2, 4.4, 4.6, 4.8 or 5.0, or any pH therebetween.

The soluble sugars produced by the enzymatic hydrolysis may be fermented by microbes. The fermentation products can include any desired products that generate value to the fermentation plant. The preferred fermentation products are ethanol, butanol and lactic acid. For ethanol production, fermentation can be carried out by one or more than one microbe that is able to ferment the sugars to ethanol. For example, the fermentation may be carried out by recombinant *Saccharomyces* yeast that has been engineered to ferment glucose, mannose, galactose and xylose to ethanol, or glucose, mannose, galactose, xylose, and arabinose to ethanol. Recombinant yeasts that can ferment xylose to ethanol are described in U.S. Pat. No. 5,789,210 (which is herein incorporated by reference). The yeast produces a fermentation broth comprising ethanol in an aqueous solution. For lactic acid production, the fermentation can be carried out by a microbe that ferments the sugars to lactic acid.

The enzyme mixtures of the invention are of a different composition than naturally occurring enzymes for cellulose hydrolysis and of those described in the prior art. The $f_{EG4}$, $f_{Swo1}$ and $f_{Cip1}$ of a native enzyme mixture secreted by *Trichoderma reesei* are 0.26, 0.20 and 0.54, respectively and thus fall outside of the preferred ranges of ratios described (see FIG. 3). The enzyme mixtures in embodiments of the present invention preferably have at least a 12% higher activity than the native enzyme mixture secreted by *Trichoderma reesei*.

EXAMPLES

The present invention will be further illustrated in the following examples.

Example 1

Purification of the Primary Cellulases, CBH1, CBH2, EG1 and EG2, and Accessory Components, EG4, Swo1 and Cip1, from *Trichoderma reesei* Cellulase A strain of *Trichoderma reesei* was grown in submerged liquid fermentation under conditions that induce cellulase production as known to those skilled in the art. (See, for example, White et al. U.S. Pat. No. 6,015,703). The crude mixture of *Trichoderma* proteins was secreted by the cells into the fermentation broth. The fungal cells were removed from the fermentation broth by filtration across a glass microfiber filter containing a Harborlite filter bed. The primary cellulases (CBH1, CBH2, EG1, EG2) were separated from the crude filtrate by ion exchange chromatography as described by Bhikhabhai et al. (1984). This step isolates EG1 and EG2. CBH1 and CBH2 were then further purified by p-aminophenyl-1-thio-β-D-cellobioside affinity chromatography as reported by Piyachomkwan et al. (1997, 1998). In order to purify the accessory components, a cellulase devoid of CBH1, CBH2 and EG1 was first separated by anion exchange chromatography. A 75 mL packed bed volume of DEAE-Sepharose was equilibrated in 10 mM Tris, 10 mM Bis-Tris, pH 8.5. The starting material was adjusted to these conditions and applied to the column at 5 mL/min. The column was then washed with 600 mL of 10 mM Tris, 10 mM Bis-Tris, pH 7.5 and then 300 mL of 10 mM Tris, 10 mM Bis-Tris, pH 6.5. Bound proteins were then eluted with 900 mL of a 0-150 mM NaCl gradient. This resulted in the elution of two major peaks in the UV absorbance profile. The first contained EG4 exclusively while the second peak contained Swo1 and Cip1. The fractions associated with the second peak were pooled, concentrated and separated by gel filtration chromatography using a BioGel P-60 column. This yielded a pure preparation of Cip1 and partially purified Swo1. Fractions containing Swo1 were treated with 1.8 M ammonium sulfate to selectively precipitate Swo1. The pellet from this treatment was separated by gel filtration chromatography as described previously. This resulted in a substantially pure form of Swo1. Purified components were concentrated and buffer exchanged into 50 mM sodium citrate, pH 5.0 using a stirred ultrafiltration cell (Amicon) and a 10 kDa NMWL polyethersulfone membrane.

Example 2

Measuring the Concentration and Purity of the Primary Cellulases and Accessory Components Protein concentrations were determined chemically using the method of Bradford et al. (*Analytical Biochemistry*, 72:248-254, (1976)). Samples of each purified protein (6 μg) were separated by SDS-PAGE and visualized post-electrophoretically by Coomassie Blue stain. The staining intensity of each band was quantified by scanning densitometry using a Chemigenius2 (Syngene) imaging system. A sample of a *Trichoderma* cellulase (12 μg total protein) was included for reference. Relative purity of the primary and accessory components was calculated by dividing the band intensity for each component by the total staining intensity measured for all bands in the same lane on the gel. EG2 lacking a carbohydrate-binding module was present in small quantities but was not considered a contaminant in this preparation. The relative purity of CBH1 and CBH2 were >95% while that for EG1, EG2, EG4, Swo1 and Cip1 was >90%.

Figure 2:
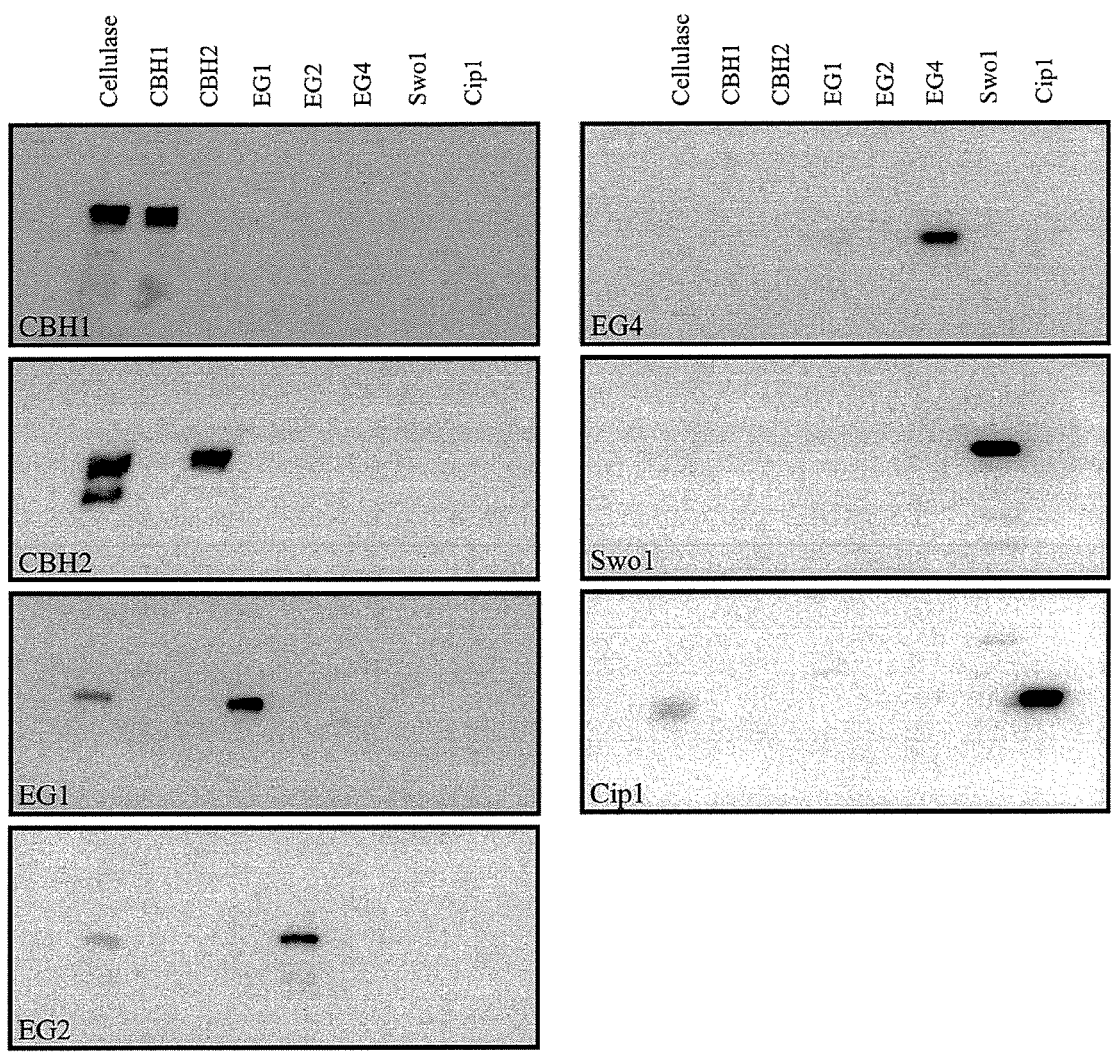
FIG. 2 shows a Western blot analysis of the purified primary and accessory components. These were separated by SDS-PAGE, electro-transferred to a PVDF membrane and visualized using component-specific polyclonal antisera. This is a more sensitive technique to detect potential cross-contamination of the purified components. This also demonstrated that all of these components were substantially free from cross-contamination of primary cellulases.

To demonstrate further that each component preparation was devoid of contaminating cellulases, purified CBH1, CBH2, EG1, EG2, EG4, Swo1 and Cip1 were analyzed by Western blotting using component-specific polyclonal antisera from rabbit (FIG. 2). Proteins were separated by 10% SDS-PAGE and transferred to a polyvinylidene fluoride (PVDF) membrane at 100 V for 1 hr using a Mini Trans-Blot® Cell from BioRad. Western blotting was done using the method of Birkett et al. (FEBS Letters, 187(2): 211-218, (1985)). The component-specific polyclonal antisera were generated using synthetic peptides, the sequence of which were based on the primary amino acid sequence of CBH1, CBH2, EG1, EG2, EG4, Swo1 or Cip1 from *Trichoderma reesei*, as known to those skilled in the art.

This example demonstrated that the purification methods used yielded substantially pure primary and accessory components. This also demonstrated the specificity of these antisera for each of these cellulase components.

Example 3

Determining the Concentrations of Primary Cellulases and Accessory Enzymes in a Commercial *Trichoderma reesei* Cellulase The relative concentrations of primary and accessory components in a commercial *Trichoderma reesei* cellulase were determined by ELISA.

Cellulase and purified component standards were diluted 1-100 μg/mL in phosphate-buffered saline, pH 7.2 (PBS) and incubated overnight at 4° C. in microtitre plates (Costar EIA—high binding). These plates were washed with PBS containing 0.1% Tween 20 (PBS/Tween) and then incubated in PBS containing 1% bovine serum albumin (PBS/BSA) for 1 hr at room temperature. Blocked microtitre wells were washed with PBS/Tween. Rabbit polyclonal antisera specific for CBH1, CBH2, EG1, EG2, EG4, Swo1 and Cip1 were diluted in PBS/BSA, added to separate microtitre plates and incubated for 2 hr at room temperature. Plates were washed and incubated with a goat anti-rabbit antibody coupled to horseradish peroxidase for 1 hr at room temperature. After washing, tetramethylbenzidine was added to each plate and incubated for 1 hr at room temperature.

The absorbance at 360 nm was measured in each well and converted into protein concentration using the CBH1, CBH2, EG1, EG2, EG4, Swo1 and Cip1 standards developed in Example 2. The relative concentration of each component was calculated by dividing these protein concentrations by the total concentration of CBH1, CBH2, EG1, EG2, EG4, Swo1 and Cip1.

The composition of the commercial *Trichoderma* cellulase is shown in Table 8.

TABLE 8

Composition of a commercial *Trichoderma* cellulase

| Component | Concentration (% of Cellulase) | Primary Components (% PC) | $f_{EG4}$ | $f_{Swo1}$ | $f_{Cip1}$ |
|---|---|---|---|---|---|
| CBH1 | 47.1 | 82.7 | 0.324 | 0.190 | 0.486 |
| CBH2 | 24.0 | | | | |
| EG1 | 5.8 | | | | |
| EG2 | 5.8 | | | | |
| EG4 | 5.6 | | | | |
| Swo1 | 3.3 | | | | |
| Cip1 | 8.4 | | | | |

The percentage of total cellulase protein accounted for by the primary cellulases (% PC) was 82.7%, where:

$$\% PC = \frac{\% CBH1 + \% CBH2 + \% EG1 + \% EG2}{\% CBH1 + \% CBH2 + \% EG1 + \% EG2 + \% EG4 + \% Swo1 + \% Cip1}$$

EG4, Swo1 and Cip1 accounted for 5.6%, 3.3% and 8.4% of total cellulase protein.

The fractional concentration of EG4 relative to all of the accessory components ($f_{EG4}$) is 5.6%/(5.6%+3.3%+8.4%)= 0.324.

The fractional concentration of Swo1 relative to all of the accessory components ($f_{Swo1}$) is 3.3%/(5.6%+3.3%+8.4%)= 0.190.

The fractional concentration of Cip1 relative to all of the accessory components ($f_{Cip1}$) is 8.4%/(5.6%+3.3%+8.4%)= 0.486.

Figure 3:
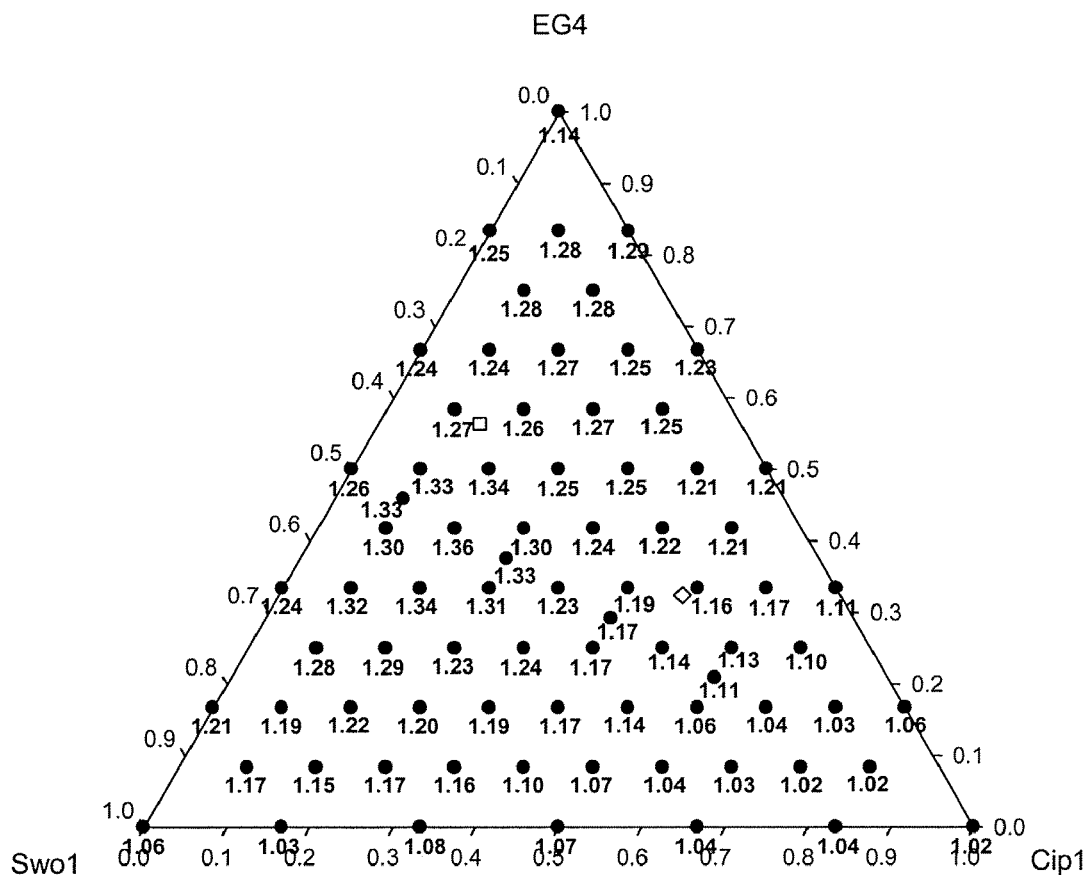
FIG. 3 shows a ternary plot representation of the enzymatic activities of a primary cellulase mixture complemented with various mixtures of EG4, Swollenin and Cip1. The primary cellulase mixture is composed of 32 wt % CBH1, 47 wt % CBH2, 17 wt % EG1 and 4 wt % EG2 (relative to the total weight of all primary cellulases). The primary cellulase mixture was combined with accessory component mixtures at a final composition consisting of 82 wt % primary cellulase mixture and 18 wt % accessory component mixture. The enzymatic activities are plotted at various fractional concentrations of EG4 ($f_{EG4}$), Swollenin ($f_{Swo1}$) and Cip1 ($f_{Cip1}$) relative to total concentration of accessory components. The activity values shown are expressed as values relative to the activity of a primary cellulase mixture without accessory components, on an equivalent protein mass basis. The accessory component composition of a commercial *Trichoderma* cellulase is shown for comparison ('Benchmark Blend'). A model optimum composition of EG4, Swo1 and Cip1 was determined by modeling the activities of the single and binary accessory component blends using Equation 1. This is labeled as the 'Model Optimum Blend'.

This accessory component composition is mapped onto the ternary plot shown in FIG. 3 and is labeled the 'Benchmark Blend'.

The concentration of CBHs relative to the entire set of primary cellulases, % CBH, is 57% (47.1%/82.7%) CBH1+ 29% (24.0%/82.7%) CBH2=86%, where:

$$\% \ CBH = \frac{\% \ CBH1 + \% \ CBH2}{\% \ CBH1 + \% \ CBH2 + \% \ EG1 + \% \ EG2}$$

The concentration of CBH2 relative to all CBH ($f_{C2}$) is 29%/(57%+29%)=0.337.

The concentration of EGs relative to the entire set of primary cellulases is 14%. The concentration of EG2 relative to all primary (EG1+EG2) EG ($f_{E2}$) is 7%/(7%+7%)=0.500.

Example 4

Measuring the Cellulose Hydrolysis Activity of Cellulase Blends on a Pretreated Lignocellulosic Feedstock Blends of EG4, Swo1 and Cip1 were prepared according to the ratios shown in Table 9. These accessory component blends were used to complement a mixture of CBH1, CBH2, EG1 and EG2. The composition of the primary cellulase blend was 32% CBH1, 47% CBH2, 17% EG1 and 4% EG2. This is optimized blend of primary cellulases identified by the methods described in U.S. Publication 2008/0057541 A1. The complementation was done such that the accessory component blend accounted for 18% (%AC) of total protein while the % PC=82%. These mixtures of primary and accessory cellulases were tested in a 0.25 mL mixed cellulose hydrolysis assay. Cellulase mixtures were diluted in citrate buffer containing 0.5% sodium benzoate, complemented with a β-glucosidase preparation from Aspergillis niger and incubated with acid pretreated wheat straw. The pretreatment was carried out as per Foody, U.S. Pat. No. 4,461,648. Incubation was at 50° C. for 24 hr and the target cellulose conversion level was greater than 70%. The enzyme activity was calculated by determining the amount of enzyme required to reach the target cellulose conversion level. These activities were normalized to the activity of the primary cellulase blend tested in the absence of accessory cellulases (% PC=100%). The total protein mass tested in all of these assays was the same. Standard errors of the cellulase activity measurements were calculated using a model comparison approach (Motulsky, H., and A. Christopoulos (2004) Fitting Models to Biological Data Using Linear and Nonlinear Regression: A Practical Guide to Curve Fitting. Oxford University Press, Inc., New York. 351 pp.). A T-test was used to compare the activity of each accessory component blend with the primary cellulase control, the benchmark blend and the optimal blend. P-values less than or equal to 0.05 were considered statistically significant.

A weighted average across the ternary blend space was applied to smooth the activity data. The normalized activity data for a given point was averaged with its six most closely neighboring points. The point in question was given a weighting w=1.00 and the six neighboring points were each given a weighting of w=0.15 in the following formula for the weighted average ($x_w$): $x_w = \Sigma w_i x_i / \Sigma w_i$ where the subscript i denotes a counting variable to sum over all 7 points described above and $x_i$ and $w_i$ indicate the normalized activity and weighting of the $i^{th}$ point respectively.

The hydrolysis activity associated with each accessory component blend is shown in Table 9 and plotted as a function of its $f_{EG4}$, $f_{Swo1}$ and $f_{Cip1}$ in FIG. 3.

TABLE 9

Relative activity of a primary cellulase mixture complemented with accessory cellulase mixtures of different $f_{EG4}$, $f_{Swo1}$ and $f_{Cip1}$.

| Blend | $f_{EG4}^a$ | $f_{Swo1}^b$ | $f_{Cip1}^c$ | Relative Activity | CI95 (95% Confidence Interval) | ΔOptimal Accessory Enzyme Blend$^d$ P-value | ΔPC Control P-value | ΔBenchmark Blend P-value |
|---|---|---|---|---|---|---|---|---|
| PC Control | — | — | — | 1.00 | 0.96-1.04 | <0.001 | 1.000 | <0.001 |
| Benchmark Blend | 0.324 | 0.190 | 0.486 | 1.16 | 1.12-1.21 | <0.001 | <0.001 | 1.000 |
| 1 | 1.000 | — | — | 1.14 | 1.12-1.17 | <0.001 | <0.001 | 0.504 |
| 2 | 0.834 | 0.083 | 0.083 | 1.28 | 1.22-1.34 | 0.059 | <0.001 | 0.002 |
| 3 | 0.667 | 0.167 | 0.166 | 1.27 | 1.22-1.33 | 0.094 | <0.001 | 0.001 |
| 4 | 0.500 | 0.250 | 0.250 | 1.25 | 1.18-1.32 | 0.009 | <0.001 | 0.055 |
| 5 | 0.334 | 0.333 | 0.333 | 1.23 | 1.17-1.28 | 0.007 | <0.001 | 0.087 |
| 6 | 0.167 | 0.417 | 0.416 | 1.17 | 1.14-1.20 | <0.001 | <0.001 | 0.519 |
| 7 | — | 0.500 | 0.500 | 1.07 | 1.03-1.10 | <0.001 | 0.017 | 0.001 |
| 8 | — | 1.000 | — | 1.06 | 1.02-1.10 | <0.001 | 0.005 | 0.036 |
| 9 | 0.083 | 0.834 | 0.083 | 1.17 | 1.15-1.18 | <0.001 | <0.001 | 0.075 |
| 10 | 0.167 | 0.666 | 0.167 | 1.22 | 1.18-1.26 | 0.002 | <0.001 | 0.094 |
| 11 | 0.250 | 0.500 | 0.250 | 1.23 | 1.15-1.32 | 0.003 | <0.001 | 0.588 |
| 12 | 0.417 | 0.167 | 0.416 | 1.22 | 1.16-1.28 | 0.011 | <0.001 | 0.040 |
| 13 | 0.500 | — | 0.500 | 1.21 | 1.15-1.27 | 0.003 | <0.001 | 0.167 |
| 14 | — | — | 1.00 | 1.02 | 0.97-1.07 | <0.001 | 0.489 | <0.001 |
| 15 | 0.083 | 0.083 | 0.834 | 1.02 | 0.99-1.06 | <0.001 | 0.100 | <0.001 |
| 16 | 0.167 | 0.167 | 0.666 | 1.04 | 0.97-1.10 | <0.001 | 0.347 | 0.003 |
| 17 | 0.250 | 0.250 | 0.500 | 1.14 | 1.11-1.16 | <0.001 | <0.001 | 0.315 |
| 18 | 0.417 | 0.416 | 0.167 | 1.36 | 1.26-1.46 | 1.000 | <0.001 | <0.001 |
| 19 | 0.500 | 0.500 | — | 1.26 | 1.21-1.30 | 0.023 | <0.001 | 0.008 |
| 20 | 0.833 | 0.167 | — | 1.25 | 1.21-1.29 | 0.013 | <0.001 | 0.003 |
| 21 | 0.667 | 0.333 | — | 1.24 | 1.18-1.29 | 0.011 | <0.001 | 0.046 |

TABLE 9-continued

Relative activity of a primary cellulase mixture complemented with accessory cellulase mixtures of different $f_{EG4}$, $f_{Swo1}$ and $f_{Cip1}$.

| Blend | $f_{EG4}{}^a$ | $f_{Swo1}{}^b$ | $f_{Cip1}{}^c$ | Relative Activity | CI95 (95% Confidence Interval) | ΔOptimal Accessory Enzyme Blend[d] P-value | ΔPC Control P-value | ΔBenchmark Blend P-value |
|---|---|---|---|---|---|---|---|---|
| 22 | 0.333 | 0.667 | — | 1.24 | 1.18-1.30 | 0.013 | <0.001 | 0.045 |
| 23 | 0.167 | 0.833 | — | 1.21 | 1.14-1.28 | 0.004 | <0.001 | 0.248 |
| 24 | — | 0.833 | 0.167 | 1.03 | 0.98-1.08 | <0.001 | 0.345 | <0.001 |
| 25 | — | 0.667 | 0.333 | 1.08 | 1.05-1.12 | <0.001 | 0.003 | 0.007 |
| 26 | — | 0.333 | 0.667 | 1.04 | 1.00-1.07 | <0.001 | 0.183 | <0.001 |
| 27 | — | 0.167 | 0.833 | 1.04 | 0.96-1.13 | <0.001 | 0.373 | 0.022 |
| 28 | 0.167 | — | 0.833 | 1.06 | 1.01-1.12 | <0.001 | 0.068 | 0.006 |
| 29 | 0.333 | — | 0.667 | 1.11 | 1.04-1.19 | <0.001 | 0.014 | 0.228 |
| 30 | 0.667 | — | 0.333 | 1.23 | 1.18-1.27 | 0.005 | <0.001 | 0.055 |
| 31 | 0.833 | — | 0.167 | 1.29 | 1.25-1.33 | 0.068 | <0.001 | <0.001 |
| 32 | 0.750 | 0.167 | 0.083 | 1.28 | 1.23-1.34 | 0.099 | <0.001 | 0.001 |
| 33 | 0.667 | 0.250 | 0.083 | 1.24 | 1.21-1.26 | 0.002 | <0.001 | 0.012 |
| 34 | 0.584 | 0.333 | 0.083 | 1.27 | 1.22-1.32 | 0.003 | <0.001 | 0.098 |
| 35 | 0.500 | 0.417 | 0.083 | 1.33 | 1.26-1.41 | 0.400 | <0.001 | <0.001 |
| 36 | 0.459 | 0.458 | 0.083 | 1.33 | 1.24-1.42 | 0.281 | <0.001 | 0.002 |
| 37 | 0.417 | 0.500 | 0.083 | 1.30 | 1.23-1.37 | 0.026 | <0.001 | 0.054 |
| 38 | 0.333 | 0.584 | 0.083 | 1.32 | 1.27-1.38 | 0.374 | <0.001 | <0.001 |
| 39 | 0.250 | 0.667 | 0.083 | 1.28 | 1.22-1.34 | 0.163 | <0.001 | <0.001 |
| 40 | 0.167 | 0.750 | 0.083 | 1.19 | 1.17-1.22 | <0.001 | <0.001 | 0.613 |
| 41 | 0.750 | 0.083 | 0.167 | 1.28 | 1.24-1.32 | 0.070 | <0.001 | <0.001 |
| 42 | 0.583 | 0.250 | 0.167 | 1.26 | 1.21-1.32 | 0.016 | <0.001 | 0.026 |
| 43 | 0.500 | 0.333 | 0.167 | 1.34 | 1.25-1.43 | 0.860 | <0.001 | <0.001 |
| 44 | 0.333 | 0.500 | 0.167 | 1.34 | 1.26-1.43 | 0.572 | <0.001 | <0.001 |
| 45 | 0.250 | 0.583 | 0.167 | 1.29 | 1.25-1.34 | 0.089 | <0.001 | <0.001 |
| 46 | 0.083 | 0.750 | 0.167 | 1.15 | 1.13-1.18 | <0.001 | <0.001 | 0.402 |
| 47 | 0.667 | 0.083 | 0.250 | 1.25 | 1.21-1.28 | 0.002 | <0.001 | 0.061 |
| 48 | 0.583 | 0.167 | 0.250 | 1.27 | 1.21-1.34 | 0.144 | <0.001 | 0.001 |
| 49 | 0.417 | 0.333 | 0.250 | 1.30 | 1.20-1.40 | 0.194 | <0.001 | 0.021 |
| 50 | 0.375 | 0.375 | 0.250 | 1.33 | 1.24-1.42 | 0.545 | <0.001 | 0.001 |
| 51 | 0.333 | 0.417 | 0.250 | 1.31 | 1.23-1.40 | 0.315 | <0.001 | 0.002 |
| 52 | 0.167 | 0.583 | 0.250 | 1.20 | 1.17-1.22 | 0.001 | <0.001 | 0.085 |
| 53 | 0.083 | 0.667 | 0.250 | 1.17 | 1.14-1.21 | <0.001 | <0.001 | 0.936 |
| 54 | 0.584 | 0.083 | 0.333 | 1.25 | 1.19-1.31 | 0.038 | <0.001 | 0.007 |
| 55 | 0.500 | 0.167 | 0.333 | 1.25 | 1.19-1.32 | 0.034 | <0.001 | 0.018 |
| 56 | 0.417 | 0.250 | 0.333 | 1.24 | 1.19-1.30 | 0.005 | <0.001 | 0.086 |
| 57 | 0.250 | 0.417 | 0.333 | 1.24 | 1.20-1.29 | 0.039 | <0.001 | 0.001 |
| 58 | 0.167 | 0.500 | 0.333 | 1.19 | 1.15-1.24 | 0.001 | <0.001 | 0.284 |
| 59 | 0.083 | 0.584 | 0.333 | 1.16 | 1.14-1.19 | <0.001 | <0.001 | 0.618 |
| 60 | 0.500 | 0.083 | 0.417 | 1.21 | 1.15-1.28 | 0.003 | <0.001 | 0.343 |
| 61 | 0.333 | 0.250 | 0.417 | 1.19 | 1.14-1.25 | 0.001 | <0.001 | 0.369 |
| 62 | 0.291 | 0.292 | 0.417 | 1.17 | 1.14-1.19 | <0.001 | <0.001 | 0.824 |
| 63 | 0.250 | 0.333 | 0.417 | 1.17 | 1.09-1.26 | 0.002 | <0.001 | 0.816 |
| 64 | 0.083 | 0.500 | 0.417 | 1.10 | 1.08-1.12 | <0.001 | 0.004 | 0.001 |
| 65 | 0.417 | 0.083 | 0.500 | 1.21 | 1.15-1.27 | 0.003 | <0.001 | 0.201 |
| 66 | 0.333 | 0.167 | 0.500 | 1.16 | 1.12-1.21 | <0.001 | <0.001 | 1.000 |
| 67 | 0.167 | 0.333 | 0.500 | 1.14 | 1.09-1.19 | 0.001 | <0.001 | 0.411 |
| 68 | 0.083 | 0.417 | 0.500 | 1.07 | 1.05-1.10 | <0.001 | 0.221 | <0.001 |
| 69 | 0.333 | 0.083 | 0.584 | 1.17 | 1.11-1.23 | 0.003 | <0.001 | 0.200 |
| 70 | 0.250 | 0.167 | 0.583 | 1.13 | 1.09-1.16 | <0.001 | <0.001 | 0.405 |
| 71 | 0.208 | 0.209 | 0.583 | 1.11 | 1.07-1.16 | <0.001 | <0.001 | 0.558 |
| 72 | 0.167 | 0.250 | 0.583 | 1.06 | 1.04-1.08 | <0.001 | 0.177 | <0.001 |
| 73 | 0.083 | 0.333 | 0.584 | 1.04 | 1.00-1.07 | <0.001 | 0.831 | <0.001 |
| 74 | 0.250 | 0.083 | 0.667 | 1.10 | 1.06-1.14 | <0.001 | 0.004 | 0.021 |
| 75 | 0.083 | 0.250 | 0.667 | 1.03 | 1.00-1.07 | <0.001 | 0.024 | 0.001 |
| 76 | 0.167 | 0.083 | 0.750 | 1.03 | 0.99-1.06 | <0.001 | 0.186 | <0.001 |
| 77 | 0.083 | 0.167 | 0.750 | 1.02 | 0.98-1.06 | <0.001 | 0.006 | <0.001 |

[a] $f_{EG4}$ = % EG4/(% EG4 + % Swo1 + % Cip1)
[b] $f_{Swo1}$ = % Swo1/(% EG4 + % Swo1 + % Cip1)
[c] $f_{Cip1}$ = % Cip1/(% EG4 + % Swo1 + % Cip1)
[d] Blend 18 as per column 1

The addition of EG4 (1.14) alone resulted in a significant improvement in cellulose hydrolysis activity (P<0.001, Table 8) compared to the primary cellulase blend (1.00). The addition of Swo1 (1.06) alone resulted in a more modest but significant (P=0.005) improvement in cellulose hydrolysis activity, compared to the primary cellulase blend. However, neither the addition of EG4 or Swo1 alone resulted in higher activity than the Benchmark Blend (1.16). The addition of Cip1 on its own (1.02) did not significantly enhance the cellulose hydrolysis activity of the enzyme blend, compared to the primary cellulase control.

The effect of the combined addition of Cip1 and Swo1 on cellulose hydrolysis activity was minimal. A blend containing equal amounts of Cip1 and Swo1 (1.07) had an activity similar to that of Swo1 alone (1.06) but was greater than Cip1 alone (1.02).

The combination of equal amounts of Swo1 and EG4 (1.26) significantly improved the activity of the cellulase mixture (P=0.008) compared to the Benchmark Blend (1.16). The combined addition of equivalent amounts of EG4 and Cip1 (1.21) improved hydrolysis performance compared to the Benchmark Blend, but this bordered on statistical significance. Without wishing to be bound by theory, EG4 may act in concert with both Swo1 and Cip1 to potentiate the cellulose hydrolysis activity of a primary cellulase mixture.

The results from the addition of individual accessory components and all binary mixtures were modeled using Equation 1 to first determine values for the synergy parameters, $\alpha$, $\beta$ and $\gamma$, and then to calculate the model optimum accessory component composition. These results are shown in Table 10.

$$A_T = f_{PC}A_{PC} + f_{EG4}A_{EG4} + f_{Swo1}A_{Swo1} + f_{Cip1}A_{Cip1} + \alpha\sqrt{f_{EG4}A_{EG4}\cdot f_{Swo1}A_{Swo1}} + \beta\sqrt{f_{EG4}A_{EG4}\cdot f_{Cip1}A_{Cip1}} + \gamma\sqrt{f_{Swo1}A_{Swo1}\cdot f_{Cip1}A_{Cip1}}$$

Equation 1:

where, $A_T$ is the total cellulose hydrolysis activity of the enzyme blend;

$f_{PC}$ is the total percentage of CBH1, CBH2, EG1 and EG2 in the enzyme blend;

$A_{PC}$ is the activity of the primary component blend alone;

$f_{EG4}$ is the fractional concentration of EG4;

$A_{EG4}$ is the activity associated with the addition of EG4 to a blend of primary cellulases in the absence of Swo1 and Cip1;

$f_{Swo1}$ is the fractional concentration of Swo1;

$A_{Swo1}$ is the activity associated with the addition of Swo1 to a blend of primary cellulases in the absence of EG4 and Cip1;

$f_{Cip1}$ is the fractional concentration of Cip1;

$A_{Cip1}$ is the activity associated with the addition of Cip1 to a blend of primary cellulases in the absence of EG4 and Swo1;

$\alpha$ represents the synergism between EG4 and Swo1;

$\beta$ represents the synergism between EG4 and Cip1;

$\gamma$ represents the synergism between Swo1 and Cip1.

TABLE 10

Determining the model optimum ratios of accessory components

| | | | Model Optimum | | |
|---|---|---|---|---|---|
| $\alpha$ | $\beta$ | $\gamma$ | $f_{EG4}$ | $f_{Swo1}$ | $f_{Cip1}$ |
| 1.14 | 1.02 | 0.29 | 0.564 | 0.314 | 0.122 |

The model optimum consists of $f_{EG4}$=0.564, $f_{Swo1}$=0.314 and $f_{Cip1}$=0.122 and is labeled as the 'Model Optimum Blend' in FIG. 3. This composition differed substantially from that of the commercial *Trichoderma* cellulase (Benchmark Blend) analyzed in Example 3.

In testing the accessory component ternary blend space, the optimal cellulose hydrolysis activity was 1.36 and was associated with a $f_{EG4}$=0.417, $f_{Swo1}$=0.416 and $f_{Cip1}$=0.167.

Both the model and empirical optimal accessory enzyme blends contained high concentrations of EG4 and Swo1 compared to lesser concentrations of Cip1. In contrast, the $f_{Cip1}$ in the commercial *Trichoderma* cellulase was 0.486, substantially greater than both the model (0.122) and empirical (0.167) optima. The cellulose hydrolysis activity associated with this ternary accessory component blend, $f_{EG4}$=0.324, $f_{Swo1}$=0.190 and $f_{Cip1}$=0.486, was 1.16, significantly lower (P<0.001) than the empirical optimum (1.36). Other blends tested in the accessory component blend space with an $f_{Cip1}$>0.333 also had significantly lower activity than the empirical optimum mixture and were not significantly better than the Benchmark Blend.

This demonstrates that the activity of a commercial *Trichoderma* cellulase on a pretreated lignocellulosic substrate can be improved upon by adjusting the ratios of the accessory components, EG4, Swo1 and Cip1. The accessory components when added on their own to a blend of primary cellulases had lower activity than the Benchmark Blend. This underscores the need to focus on multiple accessory components together acting synergistically with a primary cellulase mixture. In changing the accessory component ratios from those present in the commercial *Trichoderma* cellulase to the optimum ratios determined herein, the inventors have improved the rate of hydrolysis of lignocellulose by 17.2%.

FIG. 4 is a ternary plot modified from FIG. 3. In this graph, only accessory component mixtures that range in activity between 1.23 and 1.36 are shown, while accessory component blends with an activity less than 1.23 have been removed. These enzyme mixtures have substantially higher activity than the Benchmark Blend. The position of the Benchmark Blend is shown for reference, despite having an activity lower than 1.23. The blend space representing the accessory component mixtures shown in this figure is referred to as Zone 1 and represents preferred enzymes mixtures with activity higher than the Benchmark Blend.

FIG. 5 is a ternary plot modified from FIG. 4. In this graph, only accessory component mixtures that range in activity between 1.30 and 1.36 are shown, while accessory component blends with an activity less than 1.30 have been removed. The position of the Benchmark Blend is again shown for reference. The blend space representing the accessory component mixtures shown in this figure is referred to as Zone 2 and represents more preferred enzymes mixtures with even further enhanced activity compared to the Benchmark Blend.

The optimal mixture of accessory components consists of $f_{EG4}$=0.417, $f_{Swo1}$=0.416 and $f_{Cip1}$=0.167

Example 5

Comparing Component Mixtures Varying in Percentage of Total Primary Cellulases

Figure 6:
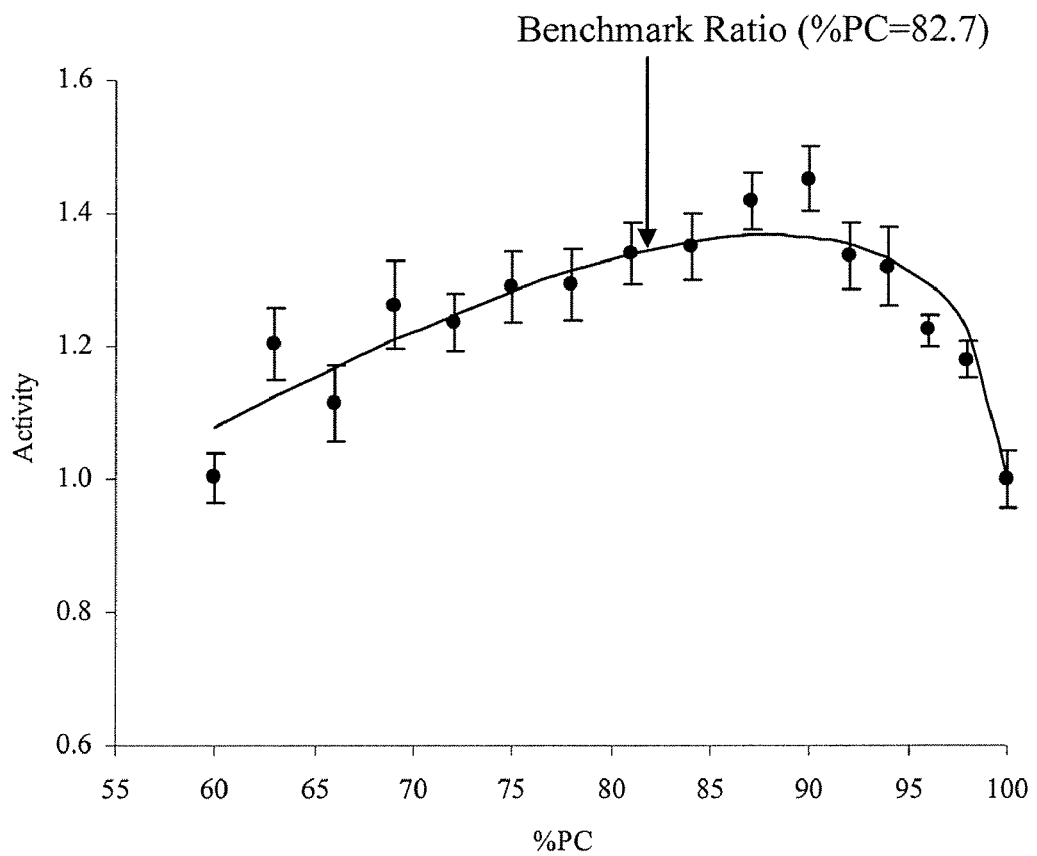
FIG. 6 shows the activities of cellulase mixtures composed of different ratios of total primary cellulase components to total accessory components, using an optimized ratio of accessory components defined in the present invention. The primary cellulase mixture is composed of 32 wt % CBH1, 47 wt % CBH2, 17 wt % EG1 and 4 wt % EG2 (relative to the total weight of all primary cellulases) while the accessory enzyme mixture consisted of 42 wt % EG4, 41 wt % Swo1 and 17 wt % Cip1 (relative to the total weight of all accessory enzyme). The combined percentage of CBH1, CBH2, EG1 and EG2 (% PC) in a commercial *Trichoderma* cellulase is labeled in this figure as the 'Benchmark Ratio'.

The hydrolysis activity of various cellulase mixtures containing primary and accessory components varying in the percentage of total primary components (% PC) was then tested. The intrinsic composition of the primary cellulase mixture was fixed, 32% CBH1, 47% CBH2, 17% EG1 and 4% EG2. The intrinsic composition of the accessory component blend was also fixed, 42% EG4, 42% Swo1 and 16% Cip1. These two mixtures were combined at different % PC and tested on pretreated wheat straw as otherwise described in Example 4. The results of these assays are shown in FIG. 6.

The % PC of the commercial Trichoderma cellulase is labeled herein as 'Benchmark Ratio' and was 82.7%. A % PC of about 90% resulted in the highest cellulose hydrolysis activity. This was slightly improved compared to the Benchmark Ratio. The cellulose hydrolysis activity decreased rapidly once the % PC was greater than about 90%. These results also demonstrate that the % PC may be decreased substantially from that present in the commercial *Trichoderma* cellulase, to approximately 75%, without marked changes in cellulose hydrolysis activity. Increasing the combined accessory component composition in a commercial *Trichoderma* cellulase may prove beneficial for the hydrolysis of other lignocellulosic feedstocks and those derived from different pretreatment conditions. This could result from changes in, without being limited by theory, the degree of polymerization, crystallinity and/or residual hemicellulose or lignin contents compared to the pretreated substrate used here.

Example 6

Measuring the Hydrolysis Activity of Primary Cellulase Blends on Pretreated Lignocellulosic Feedstock Over an Extended Period A blend of accessory components with our Benchmark values for $f_{EG4}$, $f_{Swo1}$ and $f_{Cip1}$ values from Example 3 was compared to an improved blend of accessory components with about a 17% activity improvement, as described in Example 4, in longer time course cellulose hydrolysis assays. The improved blend was of the following composition, $f_{EG4}=0.417$, $f_{Swo1}=0.416$ and $f_{Cip1}=0.167$. Both accessory component blends were added to a blend of primary cellulases, which consisted of 32% CBH1, 47% CBH2, 17% EG1 and 4% EG2. A blend of the primary cellulases was tested on its own, without the addition of accessory components, for comparison. These three blends were dosed at 6 mg enzyme per gram of cellulose and further supplemented with a β-glucosidase preparation from *Aspergillus niger* at 100 IU/g cellulose.

The blends were incubated with 25 g/L cellulose in 50 mM citrate, pH 5.0, containing 0.1% sodium benzoate at 50° C. for 194 hr with continuous orbital shaking. Aliquots of 0.7 mL were taken at various time points and the glucose concentration in the soluble portion was assayed and converted into a measure of fractional cellulose conversion. The conversion data were then fit with a rectangular hyperbola with an additional linear term using minimization of the sum of squared residuals of fit. The equation was of the following form: conversion=(max*time)/(halfmax+time)+c*time. Both sets of data were fit globally with unique max and halfmax values and a shared value of the variable c. This experiment was repeated as described on three occasions.

Figure 7:
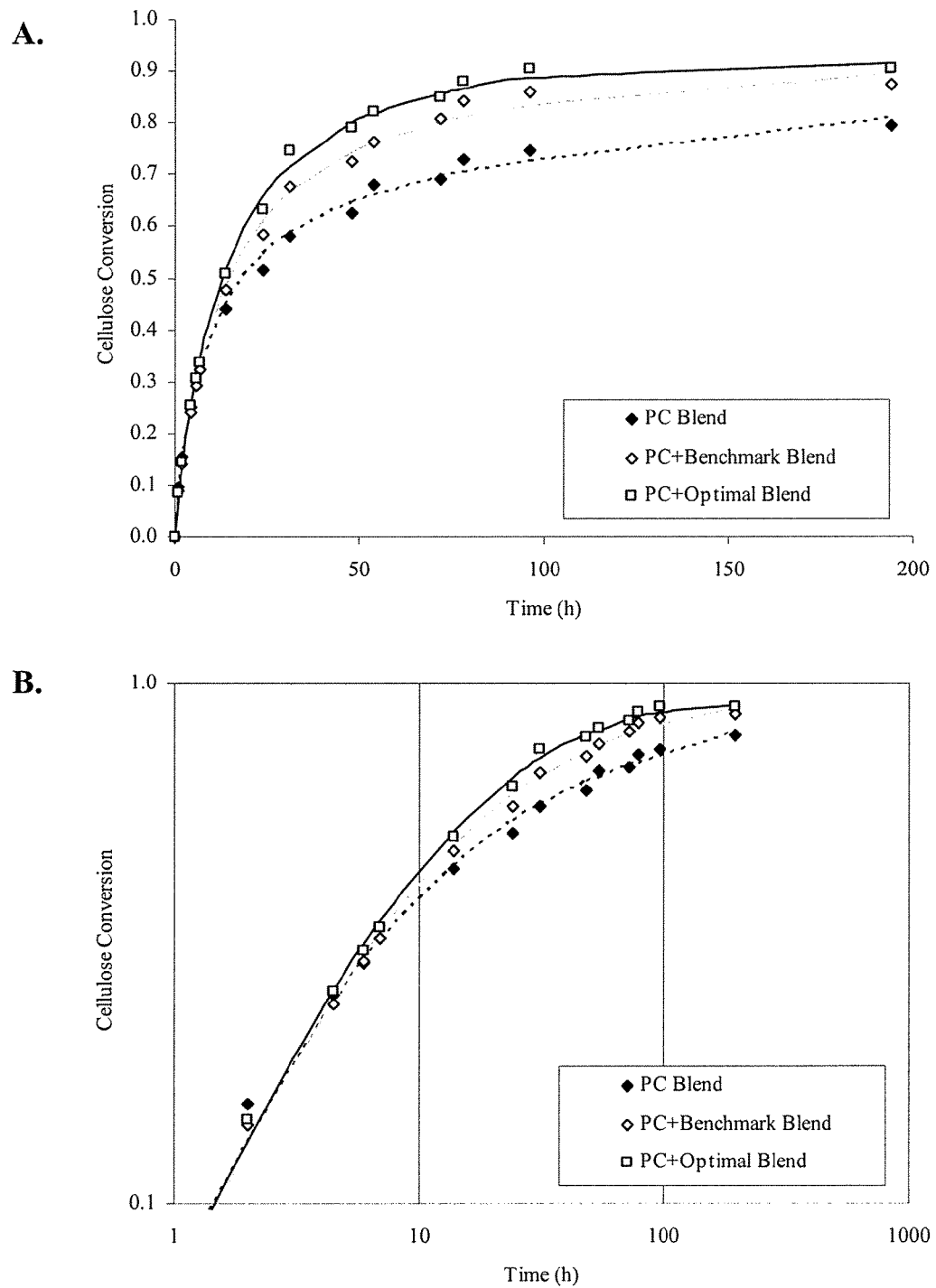
FIG. 7 shows the conversion of pretreated lignocellulosic substrate over time by different cellulase component mixtures. A benchmark blend of accessory components was compared to an optimal blend of accessory components when added to a blend of primary components. The performance of a blend of primary cellulases without EG4, Swo1 or Cip1 is shown for reference. The total protein dose of each blend used in this assay was equivalent. Both graphs (panels A and B) are of the same results, except that, in panel B, the axes have been changed to logarithmic form.

The results from a representative experiment are shown in FIG. 7. This figure demonstrates that the degree of cellulose conversion at each time point was higher for the optimal accessory component blend compared to the Benchmark Blend. The results of the three replicate experiments were further analyzed by calculating the time required to reach a target cellulose conversion of 0.75. These results are shown in Table 11. Enzyme blends containing the optimal mixture of accessory components required only 38 hr while enzyme blends containing the Benchmark Blend of accessory components required 54 hr to reach this target. This corresponded to a time savings of 30% and was statistically significant (P<0.001, Student's T-Test).

TABLE 11

Times required for enzyme blends to attain a target substrate conversion of 0.75.

|  | Time to Reach Substrate Conversion Target = 0.75 (hr) | P-Value (Relative to PC + Benchmark Blend) |
| --- | --- | --- |
| PC Blend | 108 ± 4 (n = 3) | — |
| PC + Benchmark Blend | 54 ± 5 (n = 3) | — |
| PC + Optimal Blend | 38 ± 5 (n = 3) | <0.001 |

All citations are hereby incorporated by reference.

The present invention has been described with regard to one or more embodiments. However, it will be apparent to persons skilled in the art that a number of variations and modifications can be made without departing from the scope of the invention as defined in the claims.

The embodiments of the invention in which an exclusive property or privilege is claimed are defined as follows:

1. A cellulase enzyme mixture for hydrolyzing a pretreated lignocellulosic feedstock to soluble sugars, the cellulase enzyme mixture comprising EG4, Swollenin and Cip1 accessory enzymes, wherein
   the EG4 accessory enzyme is present at a fractional concentration ($f_{EG4}$) of about 0.09 to about 0.91 (w/w) measured relative to all accessory enzymes present in the cellulase enzyme mixture,
   the Swollenin accessory enzyme is present at a fractional concentration ($f_{Swo1}$) of about 0.09 to about 0.91 (w/w) measured relative to all accessory enzymes present in the cellulase enzyme mixture, and
   the Cip1 accessory enzyme being present at a fractional concentration ($f_{Cip1}$) of 0 to about 0.42 (w/w) measured relative to all accessory enzymes present in the cellulase enzyme mixture.

2. The cellulase enzyme mixture of claim 1, wherein
   the EG4 accessory enzyme is present at a fractional concentration ($f_{EG4}$) of about 0.25 to about 0.83 (w/w) measured relative to all accessory enzymes present in the cellulase enzyme mixture,
   the Swollenin accessory enzyme is present at a fractional concentration ($f_{Swo1}$) of about 0.09 to about 0.66 (w/w) measured relative to all accessory enzymes present in the cellulase enzyme mixture, and
   the Cip1 accessory enzyme being present at a fractional concentration ($f_{Cip1}$) of 0 to about 0.33 (w/w) measured relative to all accessory enzymes present in the cellulase enzyme mixture.

3. The cellulase enzyme mixture of claim 2, wherein the cellulase enzyme mixture comprises CBH1, CBH2, EG1 and EG2 primary cellulase enzymes.

4. The cellulase enzyme mixture of claim 3, wherein the primary cellulase enzymes have a combined content within the cellulase enzyme mixture of about 70 to about 95 weight percent measured relative to the primary cellulase enzymes and accessory enzymes present in the cellulase enzyme mixture, and wherein said accessory enzymes have a combined content within the cellulase enzyme mixture of about 5 to about 30 weight percent measured relative to the primary cellulase enzymes and accessory enzymes present in the cellulase enzyme mixture.

5. The cellulase enzyme mixture of claim 4, wherein the combined content of primary cellulase enzymes within the cellulase enzyme mixture measured relative to the primary cellulase enzymes and accessory enzymes present in the cellulase enzyme mixture is about 70 to about 90 weight percent, and wherein the combined content of accessory enzymes within the cellulase enzyme mixture measured relative to the primary cellulase enzymes and accessory enzymes present in the cellulase enzyme mixture is about 10 to about 30 weight percent.

6. The cellulase enzyme mixture of claim 3, wherein the primary cellulase enzymes and accessory enzymes have a combined content of about 70 to about 100 weight percent measured relative to total protein present in the cellulase enzyme mixture.

7. The cellulase enzyme mixture of claim 3, wherein the CBH1 and CBH2 enzymes have a combined content of about 55 to about 85 weight percent and the EG1 and EG2 enzymes have a combined content of about 15 to about 45 weight percent measured relative to the combined content of CBH1, CBH2, EG1 and EG2 enzymes present in the cellulase enzyme mixture.

8. The cellulase enzyme mixture of claim 7, wherein the CBH1 and CBH2 enzymes are each present at a fractional concentration of about 0.25 to about 0.75 (w/w) measured relative to the combined content of CBH1 and CBH2 enzymes present in the cellulase enzyme mixture.

9. The cellulase enzyme mixture of claim 7, wherein the EG1 and EG2 enzymes are each present at respective fractional concentrations of about 0.35 to about 0.95 (w/w) and about 0.05 to about 0.65 (w/w) measured relative to the combined content of EG1 and EG2 enzymes present in the cellulase enzyme mixture.

10. The cellulase enzyme mixture of claim 2, wherein said EG4 enzyme is present at a fractional concentration ($f_{EG4}$) of about 0.33 to about 0.50 (w/w) measured relative to all accessory enzymes present in said enzyme mixture.

11. The cellulase enzyme mixture of claim 2, wherein said Swollenin enzyme is present at a fractional concentration ($f_{Swo1}$) of about 0.33 to about 0.58 (w/w) measured relative to all accessory enzymes present in the cellulase enzyme mixture.

12. The cellulase enzyme composition of claim 2, wherein said Cip1 is present at a fractional concentration ($f_{Cip1}$) of about 0.08 to about 0.25 (w/w) measured relative to the EG4, Swollenin and Cip1 accessory enzymes present in the cellulase enzyme mixture.

13. The cellulase enzyme mixture of claim 2, wherein the enzyme mixture is a complete blend of secreted enzymes from a microbial source, the primary cellulase enzymes and accessory enzymes making up between about 70 and about 100 weight percent of the secreted enzymes in the blend and wherein the secreted enzymes comprise additional non-cellulase enzymes that make up between >0 and 30 wt % of the secreted enzymes in the blend.

14. The cellulase enzyme mixture of claim 2, wherein the enzyme mixture comprises β-glucosidase.

15. A cellulase enzyme mixture for hydrolyzing a pretreated lignocellulosic feedstock to soluble sugars, the cellulase enzyme mixture comprising EG4, Swollenin and Cip1 accessory enzymes, wherein
the EG4 accessory enzyme is present at a fractional concentration ($f_{EG4}$) of about 0.25 to about 0.83 (w/w) measured relative to all accessory enzymes present in the cellulase enzyme mixture,
the Swollenin accessory enzyme is present at a fractional concentration ($f_{Swo1}$) of about >0 to about 0.66 (w/w) measured relative to all accessory enzymes present in the cellulase enzyme mixture, and
the Cip1 accessory enzyme being present at a fractional concentration ($f_{Cip1}$) of 0 to about 0.33 measured relative to all accessory enzymes present in the cellulase enzyme mixture.

16. A cellulase enzyme mixture for hydrolyzing a pretreated lignocellulosic feedstock to soluble sugars, the cellulase enzyme mixture comprising EG4, Swollenin and Cip1 accessory enzymes, wherein
the EG4 accessory enzyme is present at a fractional concentration ($f_{EG4}$) of about 0.25 to about 0.83 (w/w),
the Swollenin accessory enzyme is present at a fractional concentration ($f_{Swo1}$) of about 0.15 to about 0.66 (w/w), and
the Cip1 accessory enzyme being present at a fractional concentration ($f_{Cip1}$) of 0 to about 0.33 (w/w),
wherein each fractional concentration is measured relative to all of the EG4, Swollenin and Cip1 accessory enzymes present in the cellulase enzyme mixture.

17. A process for converting a pretreated lignocellulosic feedstock to soluble sugars comprising the step of enzymatically hydrolyzing the pretreated lignocellulosic feedstock with the cellulase enzyme mixture according to claim 15.

18. A method for producing the cellulase enzyme mixture according to claim 15, comprising the step of expressing the cellulase enzyme mixture from one or more microorganisms.

19. The method of claim 18, wherein the one or more microorganisms are genetically modified to adjust the levels of EG4, Swollenin, Cip1 or a combination thereof secreted by the one or more microorganisms.

20. The method of claim 19, wherein the one or more microorganisms are genetically modified by deleting one or more of the primary cellulase enzymes to adjust the expression levels of EG4, Swollenin, Cip1 or a combination thereof relative to the primary cellulases.

21. The method of claim 20, wherein the cellulase enzyme mixture is produced by conducting a fermentation at a pH of between about 2 and about 5 to adjust the expression levels of EG4, Swollenin, Cip1 or a combination thereof relative to one another or the expression levels of the accessory components relative to the primary cellulase enzymes.

22. A process for converting a pretreated lignocellulosic feedstock to soluble sugars comprising the step of enzymatically hydrolyzing the pretreated lignocellulosic feedstock with the cellulase enzyme mixture according to claim 1.

23. The process of claim 22, wherein the EG4 accessory enzyme is present at a fractional concentration ($f_{EG4}$) of about 0.25-0.83 (w/w), said Swollenin accessory enzyme is present at a fractional concentration ($f_{Swo1}$) of about 0.09 to about 0.66 (w/w), and said Cip1 accessory enzyme is present at a fractional concentration ($f_{Cip1}$) of 0 to about 0.33 w/w) measured relative to all accessory enzymes present in said enzyme mixture.

24. The process of claim 22, wherein the cellulase enzyme mixture comprises CBH1, CBH2, EG1 and EG2 primary cellulase enzymes.

25. The process of claim 23, wherein the cellulase enzyme mixture comprises CBH1, CBH2, EG1 and EG2 primary cellulase enzymes.

26. The process of claim 25, wherein the primary cellulase enzymes have a combined content within the cellulase enzyme mixture of about 70 to about 95 weight percent measured relative to the primary cellulase enzymes and accessory enzymes present in the cellulase enzyme mixture, and wherein the accessory enzymes have a combined content within the cellulase enzyme mixture of about 5 to about 30 weight percent measured relative to the primary cellulase enzymes and accessory enzymes present in the cellulase enzyme mixture.

27. The process of claim 26, wherein the combined content of primary cellulase enzymes within the cellulase enzyme mixture measured relative to the primary cellulase enzymes and accessory enzymes present in the cellulase enzyme mixture is about 70 to about 90 weight percent and wherein the combined content within the cellulase enzyme mixture of accessory enzymes present in the cellulase enzyme mixture measured relative to the primary cellulase enzymes and accessory enzymes present in the cellulase enzyme mixture is about 10 to about 30 weight percent.

28. The process of claim 25, wherein the primary cellulase enzymes and accessory enzymes have a combined content within the cellulase enzyme mixture of about 70 to about 100 weight percent measured relative to total protein present in the cellulase enzyme mixture.

29. The process of claim 25, wherein the CBH1 and CBH2 enzymes have a combined content of about 55 to about 85 weight percent and the EG1 and EG2 enzymes have a combined content of about 15 to about 45 weight percent measured relative to CBH1, CBH2, EG1 and EG2 enzymes present in the cellulase enzyme mixture.

30. The process of claim 29, wherein the CBH1 and CBH2 enzymes are each present at a fractional concentration of about 0.25 to about 0.75 (w/w) measured relative to the combined content of CBH1 and CBH2 enzymes present in the cellulase enzyme mixture.

31. The process of claim 29, wherein the EG1 and EG2 enzymes are each present at respective fractional concentrations of from about 0.35 to about 0.95, (w/w) and from about 0.05 to about 0.65 (w/w) measured relative to the combined content of EG1 and EG2 enzymes present in the cellulase enzyme mixture.

32. The process of claim 23, wherein the EG4 enzyme is present at a fractional concentration ($f_{EG4}$) of about 0.33 to about 0.50 (w/w) measured relative to all accessory enzymes present in the cellulase enzyme mixture.

33. The process of claim 23, wherein the Swollenin enzyme is present at a fractional concentration ($f_{Swo1}$) of about 0.33 to about 0.58 (w/w) measured relative to all accessory enzymes present in the cellulase enzyme mixture.

34. The process of claim 23, wherein the Cip1 is present at a fractional concentration ($f_{Cip1}$) of about 0.08 to about 0.25 (w/w) measured relative to the EG4, Swollenin and Cip1 accessory enzymes present in the cellulase enzyme mixture.

35. The process of claim 25, wherein the primary cellulase enzymes and accessory enzymes are from a fungal source.

36. The process of claim 35, wherein the fungal source is an *Ascomycete* or *Basidomycete* fungus.

37. The process of claim 36, wherein the fungal source is selected from the group consisting of *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Fusarium* ssp., *Penicillium* ssp., *Magnaporthe* ssp., and *Phanerochaete* ssp.

38. The process of claim 37, wherein the fungal source is *Trichoderma reesei*.

39. The process of claim 25, wherein the primary cellulase enzymes and accessory enzymes are obtained from an organism by expressing coding sequences which are endogenous to the organism.

40. The process of claim 25, wherein the primary cellulase enzymes and accessory enzymes are obtained from an organism by expressing coding sequences which are heterologous to the organism.

41. The process of claim 25, wherein the primary cellulase enzymes and accessory enzymes are produced by expression in *Trichoderma reesei*.

42. The process of claim 23, wherein in the step of enzymatically hydrolyzing, at least 80 wt % of cellulose in the pretreated lignocellulosic feedstock is converted to soluble sugars.

43. The process of claim 42, wherein the step of enzymatically hydrolyzing is followed by a step of fermentation to produce ethanol, lactic acid, butanol, or a combination thereof from the soluble sugars.

44. The process of claim 25, wherein the cellulase enzyme mixture is a complete blend of secreted enzymes from a microbial source, the primary cellulase enzymes and accessory enzymes making up between about 70 and about 100 wt % of the secreted enzymes in the blend and wherein the secreted enzymes comprise additional non-cellulase enzymes that make up between >0 and about 30 wt % of the secreted enzymes in the blend.

45. The process of claim 23, wherein the cellulase enzyme mixture comprises β-glucosidase.

* * * * *